(12) United States Patent
Atwater et al.

(10) Patent No.: US 12,223,723 B2
(45) Date of Patent: Feb. 11, 2025

(54) FISH MEASUREMENT STATION KEEPING

(71) Applicant: TidalX AI Inc, San Ramon, CA (US)

(72) Inventors: Joel Fraser Atwater, Danville, CA (US); Barnaby John James, Campbell, CA (US); Matthew Messana, Sunnyvale, CA (US)

(73) Assignee: TidalX AI Inc., Mountain View, CA (US)

( * ) Notice: Subject to any disclaimer, the term of this patent is extended or adjusted under 35 U.S.C. 154(b) by 0 days.

(21) Appl. No.: 17/391,392

(22) Filed: Aug. 2, 2021

(65) Prior Publication Data

US 2021/0374427 A1    Dec. 2, 2021

Related U.S. Application Data

(63) Continuation of application No. 16/701,853, filed on Dec. 3, 2019, now Pat. No. 11,113,539, which is a
(Continued)

(51) Int. Cl.
*G06V 20/52* (2022.01)
*A01K 61/10* (2017.01)
(Continued)

(52) U.S. Cl.
CPC .............. *G06V 20/52* (2022.01); *A01K 61/10* (2017.01); *A01K 61/95* (2017.01); *G06T 7/20* (2013.01); *H04N 23/667* (2023.01)

(58) Field of Classification Search
CPC ...... A01K 61/10; A01K 61/95; A01K 29/005; A01K 61/13; A01K 61/60; A01K 61/80;
(Continued)

(56) References Cited

U.S. PATENT DOCUMENTS 6,097,424 A * 8/2000 Zernov ................. H04N 7/183
348/81
6,119,630 A * 9/2000 Lobsiger .............. G01N 33/186
348/81
(Continued)

FOREIGN PATENT DOCUMENTS

CL    2019000039 A1    3/2019
CN    102297865 B    2/2013
(Continued)

OTHER PUBLICATIONS

Office action Chile Appln. No. 202001744, dated Sep. 27, 2021, 13 pages (with English summary).
(Continued)

*Primary Examiner* — Tom Y Lu
(74) *Attorney, Agent, or Firm* — Fish & Richardson P.C.

(57) ABSTRACT

A fish monitoring system deployed in a particular area to obtain fish images is described. Neural networks and machine-learning techniques may be implemented to periodically train fish monitoring systems and generate monitoring modes to capture high quality images of fish based on the conditions in the determined area. The camera systems may be configured according to the settings, e.g., positions, viewing angles, specified by the monitoring modes when conditions matching the monitoring modes are detected. Each monitoring mode may be associated with one or more fish activities, such as sleeping, eating, swimming alone, and one or more parameters, such as time, location, and fish type.

20 Claims, 11 Drawing Sheets

Related U.S. Application Data continuation of application No. 15/970,131, filed on May 3, 2018, now Pat. No. 10,534,967.

(51) Int. Cl.
  *A01K 61/95* (2017.01)
  *G06T 7/20* (2017.01)
  *H04N 23/667* (2023.01)

(58) Field of Classification Search
  CPC ...... A01K 61/90; G06K 9/00771; G06T 7/20; H04N 5/23245; G16H 40/67; Y02A 40/81
  See application file for complete search history.

(56) References Cited

U.S. PATENT DOCUMENTS

| | | | |
|---|---|---|---|
| 9,541,645 | B2 | 1/2017 | Yamaguchi |
| 9,817,120 | B2 | 9/2017 | Ferretti |
| 9,992,987 | B2 | 6/2018 | Bailey |
| 10,856,520 | B1 | 12/2020 | Kozachenok et al. |
| 11,113,539 | B2 * | 9/2021 | Atwater ............... A01K 61/95 |
| 2006/0018197 | A1 | 1/2006 | Burczynski et al. |
| 2010/0198023 | A1 | 8/2010 | Yanai et al. |
| 2015/0302241 | A1 | 10/2015 | Eineren et al. |
| 2015/0313199 | A1 | 11/2015 | Castaneda et al. |
| 2016/0249036 | A1 | 8/2016 | Son |
| 2017/0150701 | A1 | 6/2017 | Gilmore et al. |
| 2018/0132459 | A1 | 5/2018 | Baba et al. |
| 2018/0303073 | A1 | 10/2018 | Jans |
| 2019/0170720 | A1 * | 6/2019 | Howard ............... G06F 18/214 |
| 2019/0228218 | A1 | 7/2019 | Barnaby et al. |
| 2020/0107524 | A1 | 4/2020 | Messana et al. |
| 2020/0155882 | A1 | 5/2020 | Tohidi et al. |
| 2020/0288678 | A1 | 9/2020 | Howe et al. |

FOREIGN PATENT DOCUMENTS

| | | | | |
|---|---|---|---|---|
| CN | 104113739 | A * | 10/2014 | ............ H04N 7/18 |
| CN | 204229274 | U | 3/2015 | |
| CN | 105719424 | A | 6/2016 | |
| CN | 107135988 | A | 9/2017 | |
| CN | 107423745 | | 12/2017 | |
| CN | 108040948 | | 5/2018 | |
| CN | 207870096 | | 9/2018 | |
| EP | 2244934 | | 11/2010 | |
| EP | 3484283 | | 5/2019 | |
| JP | 1997251192 | | 9/1997 | |
| JP | 2002171853 | | 6/2002 | |
| JP | 2017-181766 | * | 10/2017 | ............ G03B 17/56 |
| NO | 300401 | | 5/1997 | |
| NO | 20160199 | | 8/2017 | |
| NO | 345829 | | 10/2019 | |
| WO | WO 1990/007874 | | 7/1990 | |
| WO | WO 1997/019587 | | 6/1997 | |
| WO | WO 2009/008733 | | 1/2009 | |
| WO | WO 2009/067025 | * | 5/2009 | ............ G01R 31/50 |
| WO | WO 2009/097057 | | 8/2009 | |
| WO | WO2012081990 | | 6/2012 | |
| WO | WO-2014098614 | A1 * | 6/2014 | ............ A01K 61/001 |
| WO | WO 2014/179482 | | 11/2014 | |
| WO | WO 2016/023071 | | 2/2016 | |
| WO | WO2017137896 | | 8/2017 | |
| WO | WO 2018/011744 | | 1/2018 | |
| WO | WO2018011745 | | 1/2018 | |
| WO | WO 2019/002881 | | 1/2019 | |
| WO | WO 2019/121851 | | 6/2019 | |
| WO | WO 2019/188506 | | 10/2019 | |
| WO | WO 2019/232247 | | 12/2019 | |
| WO | WO 2020/046524 | | 3/2020 | |
| WO | WO 2020/072438 | | 4/2020 | |
| WO | WO 2020/132031 | | 6/2020 | |
| WO | WO 2021/006744 | | 1/2021 | |
| WO | WO 2021/030237 | | 2/2021 | |
| WO | WO 2022/010815 | | 1/2022 | |

OTHER PUBLICATIONS

PCT International Preliminary Report on Patentability in International Appln. No. PCT/US2019/028743, dated Nov. 3, 2020, 8 pages.
PCT International Search Report and Written Opinion in International Appln. No. PCT/US2019/028743, dated Jul. 31, 2019, 33 pages.
PCT International Search Report and Written Opinion in International Appln. No. PCT/US2021/016387, dated May 3, 2021, 14 pages.
Extended Search Report in European Appln. No. 22151132.2, dated May 2, 2022, 10 pages.
Decision to Grant a Patent in Japanese Appln. No. 2020-531499, dated Jun. 29, 2022, 5 pages (with English translation).
International Search Report and Written Opinion in International Appln No. PCT/US2022/022837, dated Aug. 2, 2022, 14 pages.
International Search Report and Written Opinion in International Appln No. PCT/US2022/018651, dated Jun. 22, 2022, 14 pages.
International Search Report and Written Opinion in International Appln No. PCT/US2022/021683, dated Jun. 27, 2022, 14 pages.
International Search Report and Written Opinion in International Appln No. PCT/US2022/022250, dated Jul. 6, 2022, 15 pages.
International Search Report and Written Opinion in International Appln No. PCT/US2022/022492, dated Jun. 28, 2022, 13 pages.
International Search Report and Written Opinion in International Appln No. PCT/US2022/022589, dated Jul. 7, 2022, 12 pages.
International Search Report and Written Opinion in International Appln No. PCT/US2022/023831, dated Jul. 8, 2022, 13 pages.
International Preliminary Report on Patentability in International Appln. No. PCT/US2020/059829, dated May 27, 2022, 11 pages.
International Search Report and Written Opinion International Appln No. PCT/US2020/059829, dated Feb. 25, 2021, 18 pages.
Meidell et al., "FishNet: A Unified Embedding for Salmon Recognition," Thesis for Master's degree in Artificial Intelligence, Norwegian University of Science and Technology, Jun. 2019, 86 pages.
Moskvyak et al., "Robust Re-identification of Manta Rays from Natural Markings by Learning Pose Invariant Embeddings," CoRR, Feb. 2019, arXiv:1902.10847v1, 12 pages.
Office Action in Canadian Appln. No. 3,087,370, dated May 19, 2022, 4 pages.
Qiu et al., "Improving Transfer Learning and Squeeze-and-Excitation Networks for Small-Scale Fine-Grained Fish Image Classification," IEEE ACCESS, Dec. 2018, 6(31):78503-78512.
Stein et al., "Consistent melanophore spot patterns allow long-term individual recognition of Atlantic salmon Salmo Salar," Journal of Fish Biology, Nov. 2017, 91(6):1699-1712.
Office Action in Canadian Appln. No. 3,087,370, dated Mar. 21, 2023, 5 pages.
Office Action in European Appln. No. 19727154.7, dated Feb. 22, 2023, 8 pages.
Office Action in European Appln. No. 19727154.7, dated Oct. 2, 2023, 7 pages.
Office Action in Canadian Appln. No. 3,087,370, dated Jan. 8, 2024, 6 pages.

* cited by examiner

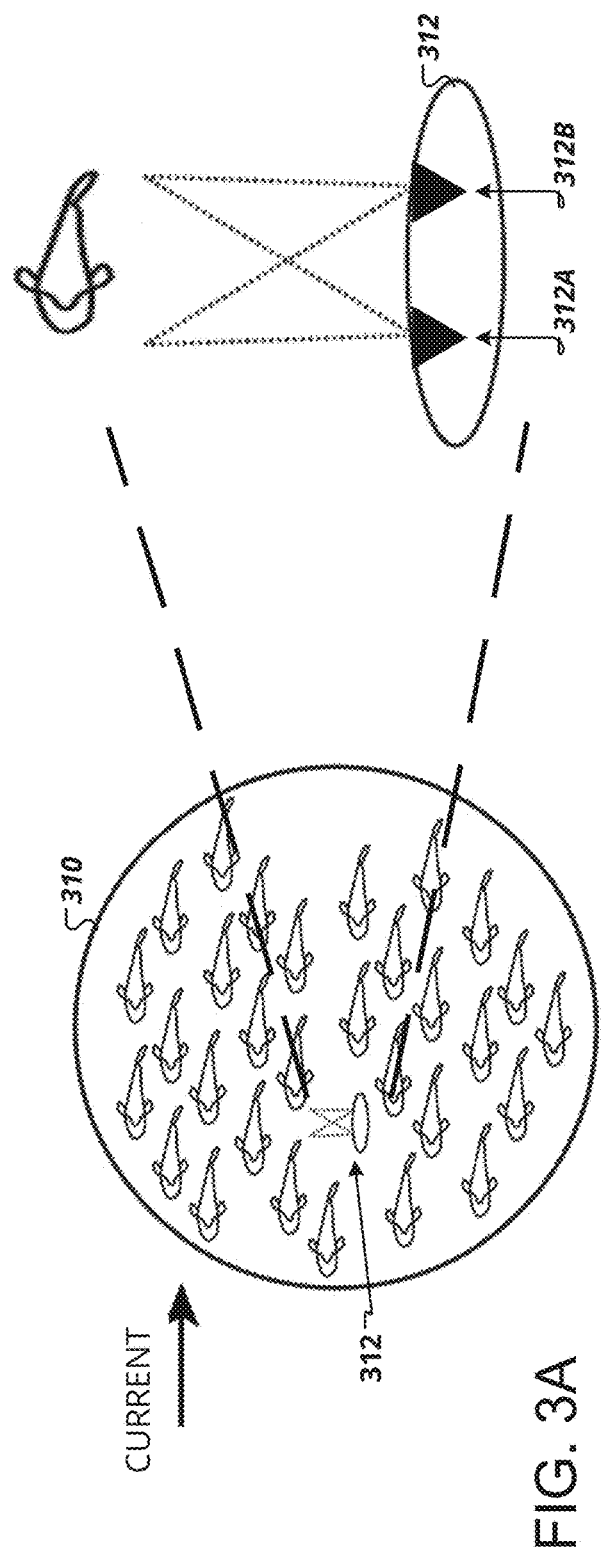
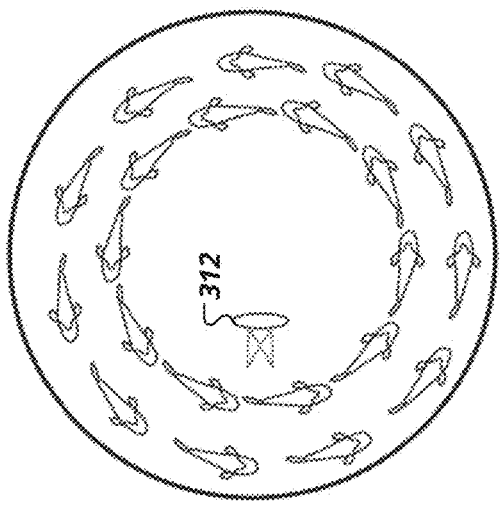
FIG. 3A
FIG. 3B

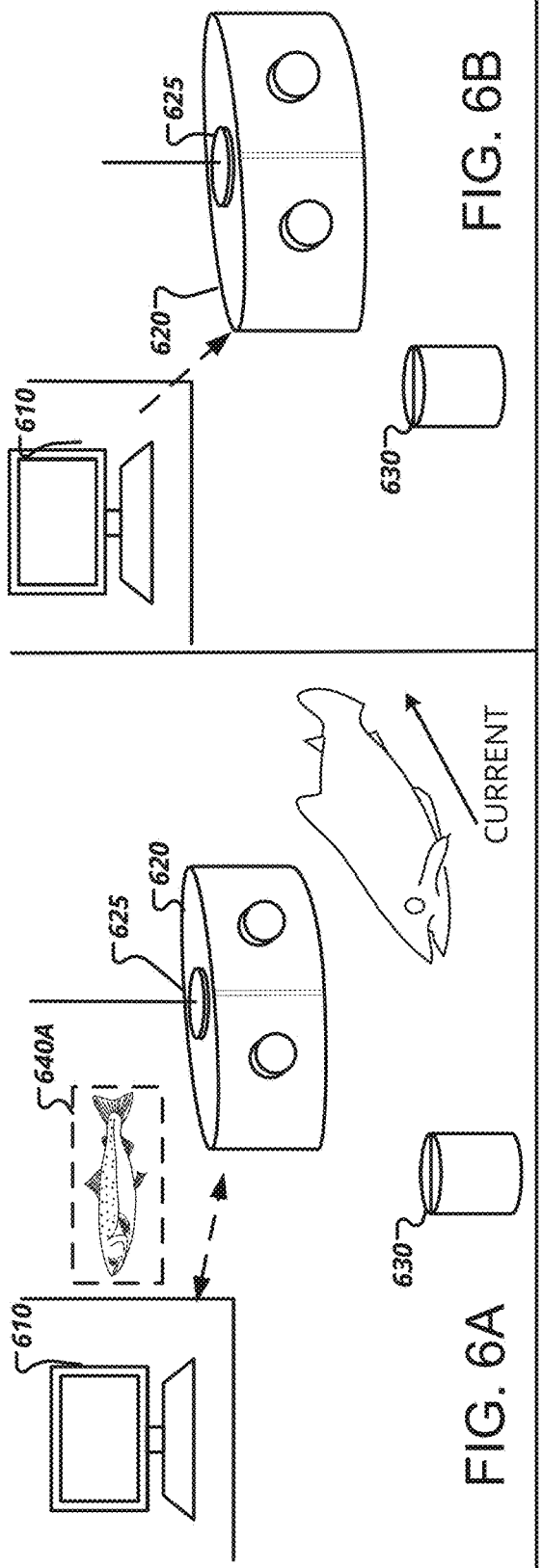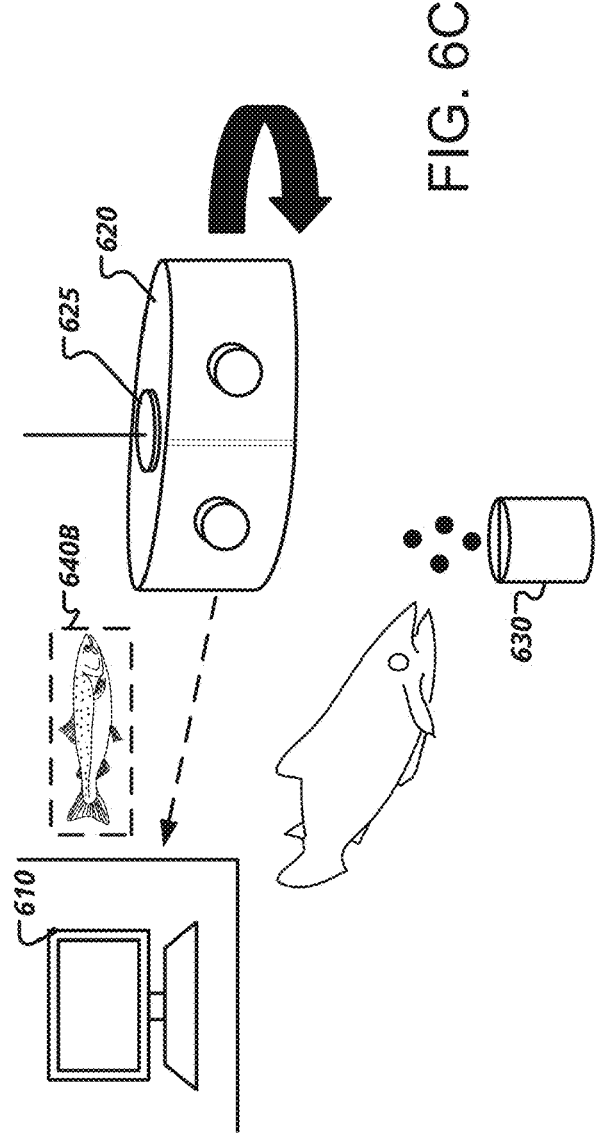

FISH MEASUREMENT STATION KEEPING

CROSS-REFERENCE TO RELATED APPLICATIONS

This application is a continuation of U.S. application Ser. No. 16/701,853, filed Dec. 3, 2019, which is a continuation of U.S. patent application Ser. No. 15/970,131, filed May 3, 2018, now allowed. The contents of the prior applications are incorporated herein by reference in their entirety.

FIELD

This disclosure generally relates to the marine monitoring systems.

BACKGROUND

Researchers and firm farm operators face several challenges in observing and recording behavior of fish. A manual process of observing a sample set of fish is often used to estimate fish characteristics. However, such a process is often time-consuming, inaccurate, expensive, and has several limitations such as decreased accessibility during certain times of the day or during adverse weather conditions.

SUMMARY

In general, innovative aspects of the subject matter described in this specification relate to fish monitoring.

Aspects of the subject matter described in this specification can be embodied in a system. The system includes one or more computing devices and one or more storage devices that store instructions which, when executed by the one or more computing devices, cause the one or more computing devices to perform operations. The operations include: receiving data indicative of (I) one or more conditions at one or more locations in a determined area of an underwater fish pen, and (II) one or more parameters for monitoring one or more objects in the determined area of the underwater fish pen; determining a monitoring mode, from among multiple monitoring modes, for a camera system in the determined area of the underwater fish pen based on the one or more conditions and the one or more parameters; configuring the camera system according to the determined monitoring mode to align one or more cameras in the camera system with a target profile of the one or more objects; and obtaining a set of one or more images in response to configuring the camera system according to the determined monitoring mode. The set of one or more images includes images of the one or more objects in the determined area of the underwater fish pen.

Implementations may each optionally include one or more of the following features. For instance, in some implementations, receiving data indicative of the one or more conditions at the one or more locations in the determined area of the underwater fish pen includes one or more of: receiving image data from the one or more cameras, receiving data from a user indicating a swimming pattern or swimming behavior of the one or more objects, and receiving environmental data indicating environmental conditions in the determined area from one or more sensors that include a light sensor, thermometer, salinity sensor, optical sensor, motion sensor, and current sensor.

In some implementations, the one or more conditions include a movement of an object, an orientation of an object, a direction of current, a strength of the current, a salinity level, a luminosity, a temperature level, a depth level, a pressure level, an oxygen level, and a topology of the determined area.

In some implementations, receiving data indicative of the one or more parameters for monitoring the one or more objects in the determined area of the underwater fish pen includes one or more of: obtaining data indicative of an activity or behavior in which the one or more objects are engaged in, and obtaining data indicative of a type of object of interest.

In some implementations, the behavior includes one or more of sleeping, eating, swimming alone, swimming in a school, swimming in position, and moving according to a particular movement pattern. The objects include one or more of: fish and the type of object is a species of fish or an identification of a particular fish; and parasites and the type of object is a species of parasite or an identification of a particular parasite.

In some implementations, determining the monitoring mode for the camera system in the determined area of the underwater fish pen based on the one or more conditions and the one or more parameters includes: determining one or more monitoring modes that map to the one or more conditions, the one or more parameters, and the one or more locations; determining a score for each of the one or more monitoring modes; and selecting the monitoring mode having the highest score among the scores for the one or more monitoring modes.

In some implementations, configuring the camera system according to the determined monitoring mode to align the one or more cameras in the camera system with the target profile of the one or more objects includes controlling the camera system to position the one or more cameras in the camera system (i) at approximately a perpendicular angle to a body of the one or more objects proximate to the one or more cameras, and (ii) to be approximately horizontal to the body of the one or more objects.

In some implementations, the one or more objects include fish, and the operation of controlling the camera system to position the one or more cameras in the camera system to be approximately horizontal to the body of the one or more objects includes: controlling the one or more cameras to move upward or downward in the determined area of the underwater fish pen until the one or more cameras are approximately parallel to a fish proximate to the one or more cameras, and a line extending from the one or more cameras to the fish is parallel to a top surface of water in the fish pen; and controlling the one or more cameras to move laterally such that all key points on at least one side of the body of the fish proximate to the one or more cameras are completely visible in a lens of each of the one or more cameras at the same time. The target profile of the fish includes all the key points on at least one side of the body of the fish, the key points correspond to an eye, nostril, gill plate, operculum, auxiliary bone, pectoral fin, lateral line, dorsal fin, adipose fin, pelvic fin, anal fin, and caudal fin of the fish In some implementations, configuring the camera system includes activating a first set of cameras in the camera system and deactivating a second set of cameras based on the determined monitoring mode.

In some implementations, the operations further include in response to obtaining the set of one or more images, determining a quality factor of the one or more images and determining whether the quality factor satisfies a quality threshold. In response to the quality factor not satisfying the quality threshold, the one or more computing devices receive additional data, reconfiguring the camera system based on the additional data, and obtain a second set of one or more images of the one or more objects. The additional data includes a second set of data indicative of (I) one or more conditions at the one or more locations in the determined area of the underwater fish pen, and (II) one or more parameters for monitoring the one or more objects in the determined area of the underwater fish pen. In response to the quality factor satisfying the quality threshold, the one or more computing devices obtain a second set of images of the objects without reconfiguring the camera system.

Other aspects include corresponding methods, systems, apparatus, computer-readable storage media, and computer programs configured to implement the operations of the above-noted methods.

The above-noted aspects and implementations further described in this specification may offer several advantages. For example, an automated and dynamic manner of observing fish is described. Through the use of machine-learning techniques and neural networks, the system may adjust camera positions and settings and modify monitoring modes so that obtained images may be of high quality, e.g., without blurriness and incomplete images of fish. Since the modes may be customized for particular activities, researchers do not have to filter through thousands of images to identify which images are pertinent to the activity they are researching. Rather, only relevant data is provided to the researchers, thereby providing improved efficiency for computer, storage, and network resources.

The obtained images may be used by a computing device to execute additional operations. For example, the obtained images may be used by the computing device to identify and extract features on fish, to profile fish, and to classify and track fish behavior. The obtained images may be used to monitor conditions in a determined area and to control devices in the determined area. For example, if a feeding device is used to feed fish, the computing device may turn off the feeding device if no more fish are eating the food in obtained images. This prevents food waste and overeating of fish.

The details of one or more aspects described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 3A and 3B depict a top view of a net pen system.

FIGS. 6A-6C depict exemplary implementations of the fish monitoring system operating in different modes.

Like reference numbers and designations in the various drawings indicate like elements.

DETAILED DESCRIPTION

Fish monitoring systems can be deployed in a determined area, such as a net pen system, to monitor fish. High-quality images of fish may be obtained when a camera system in the fish monitoring system is positioned substantially horizontal to the fish, e.g., the camera system has a viewing angle that is not below or above a fish, and when a fish is swimming in a direction perpendicular to a lens of the camera system. However, fish swimming patterns may change due to conditions such as temperature, lighting, and current direction, in the determined area and due to timings of fish activities such as resting, eating, or schooling. To implement a reliable and efficient fish monitoring system to obtain high quality, unobstructed images of fish, the camera system should be able to adapt to the varying conditions in the determined area and the fish swimming patterns. The fish monitoring system may be used to monitor an individual fish, multiple fish, or an entire population of fish in a given area.

According to implementations, neural networks and machine learning techniques may be implemented to periodically train the fish monitoring systems to capture high-quality images of fish based on the conditions in the determined area. As described in this specification, trained monitoring systems may obtain high-quality images, e.g., unobstructed images of fish in the determined area with minimal user intervention. As discussed in detail below, the obtained images of fish include a complete horizontal profile of a fish in which a fish's full body and all its key points are visible, and the flatness or straightness of its body can be estimated.

The monitoring systems may have one or more monitoring modes, and camera systems may be configured by certain settings, e.g., positions, viewing angles, as indicated by the monitoring modes. Each monitoring mode may be associated with a fish type and a fish activity such as sleeping, eating, swimming alone, swimming in a school, swimming in position, and moving according to a particular movement pattern, e.g., flexing, stretching, locomotion. The monitoring modes may be configured according to time and location data such as particular times of the day or at particular locations in the determined area. The monitoring modes may also be used to track one or more fish and determine characteristics of fish, such as the shape, size, or mass of a fish.

Aspects of the disclosed subject matter are described in further detail with respect to the figures.

Figure 1:
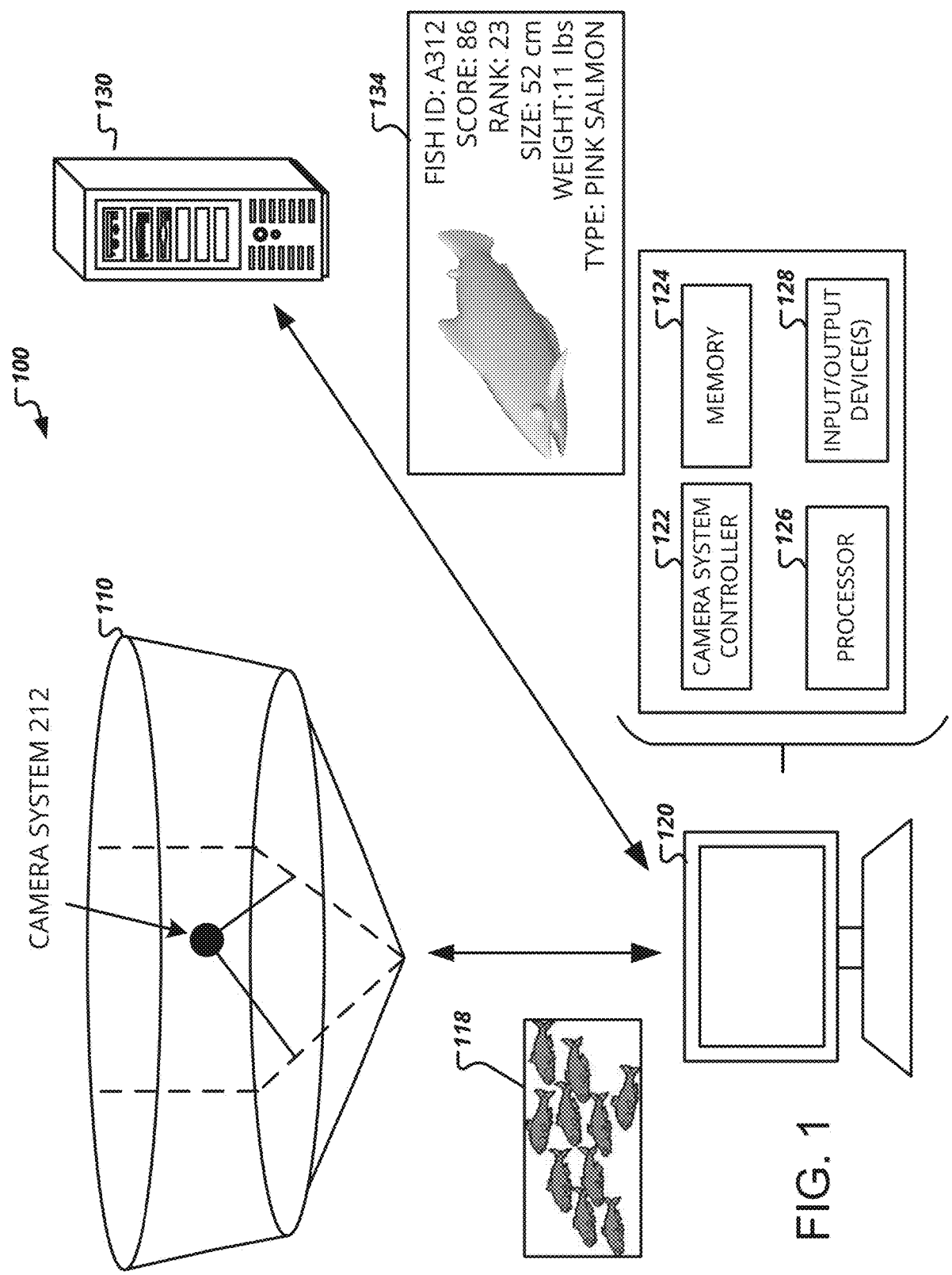
FIG. 1 depicts an exemplary system for monitoring fish.

FIG. 1 depicts an exemplary system 100 for monitoring fish. The system 100 may include a net pen system 110, a computing device 120, and a server 130. The net pen system 110 may include a fish monitoring system that includes filters and multiple sensors, such as light sensors, thermometers, salinity sensors, motion sensors, current sensors, and a camera system 112. Various implementations of the net pen system 110 may be used. Exemplary implementations of the fish thank 110 are described below with reference to FIGS. 2A-2F.

The camera system 112 may include one or more video/photographic cameras, stereo cameras, or optical sensing devices configured to capture images. For instance, the camera system 112 may be configured to capture images of one or more fish at various depths and lighting conditions in the net pen system 110. The camera system 112 may be configured to capture single, static images of fish and also video images of fish in which multiple images of fish may be periodically captured.

The camera system 112 may be triggered by several different types of techniques. For instance, motion sensors may be built into the camera system 112 and used to trigger the camera system 112 to capture one or more images when motion is detected. In some implementations, the camera system 112 is configured to receive a command to capture an image from the computing device 120 or a sensor.

In some examples, the camera system 112 may trigger integrated or external illuminators, e.g., Infrared, Z-wave controlled "white" lights, lights controlled by the computing device 120, to improve image quality when light is deficient. An integrated or separate light sensor may be used to determine if illumination is desired. Activating the illuminators may result in increased image quality.

The camera system 112 may be programmed according to any combination of time/day schedules, system activation commands, or other parameters to determine when images should be captured. The camera system 112 may enter a low-power mode when not capturing images. In some cases, the camera system 112 may be powered by internal, replaceable batteries. In some cases, the camera system 112 may employ a small solar cell to recharge the battery when light is available.

The camera system 112 may be connected to computing device 120 through cables, and data, such as image 118, may be communicated to the computing device 120 through the cables. The computing device 120 may transmit commands to the camera system 112 through the cables. In general, various implementations of the camera system 112 may be used. Exemplary implementations of the camera system 112 are described further below with reference to FIGS. 4A-4E.

The computing device 120 may include a camera system controller 122, memory 124, processor 126, and input/output devices 128. The camera system controller 122 may include a neural network and may be trained using training data and various machine-learning methods. The training data may include various images of fish with variations. For example, the training data may include images of fish having the same or different types of features, e.g., fins, tails, and properties, e.g., shape, size, color, of the features. In some cases, variations in the location of a fish in an image, for example, in the center, on the side, or on the border of an image, may be used. Images of fish from different angles and engaging in different activities may be used as training data. For example, images of a fish facing a camera, being perpendicular to the camera, or swimming away from the camera may be used as training data. Images of fish captured at various camera viewing angles may be used as training data.

Based on the training, the camera system controller 122 may predict probable locations of the fish features and variations in the properties of the features, such as a shape, size, and color of the feature. The camera system controller 122 may also be trained to determine how the variations in the shape and size of a fish and locations of features in the fish affect the weight of a fish. In some implementations, the positions and orientation of one or more camera systems may be determined based on the training.

Memory 124 may be implemented as one or more mass storage devices, for example, magnetic, magneto optical disks, optical disks, EPROM, EEPROM, flash memory devices, and may be implemented as internal hard disks, removable disks, magneto optical disks, CD ROM, or DVD-ROM disks for storing data. In some implementations, the memory 124 may store fish profile data, which may include size, shape, weight, score, and ranking data associated with each profiled fish. The fish profile data may also include one or more images and 3D models of a fish. In some implementations, memory 124 may store training data for training the camera system controller 122 and rules for training the camera system controller 122 and neural networks.

Input/output devices 128 may include input devices such as a keyboard, a pointing device, a mouse, a stylus, and/or a touch sensitive panel, e.g., a touch pad or a touch screen. Output devices may include displays, screens, speakers, and, in general, any device that can output digital data. Input/output devices 128 may also include a transceiver that includes a transmitter and a receiver and may be utilized to communicate with server 130. The transceiver may include amplifiers, modulators, demodulators, antennas, and various other components. The transceiver may transfer or route data between devices connected to the server 130. The transceiver may route data communicated between the net pen system 110 and server 130 and between computing device 120 and server 130. For example, after capturing a fish image and determining the fish's weight, shape, size, or 3D model, as described below, the computing device 120 may transmit, via transceiver, fish profile information 134 such as one or more of a fish identification, data for generating a 3D model of the fish, one or more images of the fish, a fish type, a fish size, a fish weight, and a score or rank of the fish to a server 130.

Processor 126 may be coupled to the camera system controller 122, memory 124, and input/output device 128 for executing instructions to implement the methods described is this specification. In some implementations, executable instructions may be stored in the memory device 110. The processor 126 may be programmed by encoding an operation as one or more executable instructions and providing the executable instructions in the memory device 110. The processor 126 may include one or more processing units, e.g., without limitation, in a multi-core configuration. The term processing unit, as used herein, refers to microprocessors, microcontrollers, reduced instruction set circuits (RISC), application specific integrated circuits (ASIC), logic circuits, and any other circuit or device capable of executing instructions to perform operations described herein. In some implementations, the camera system controller 122 may be implemented as part of the processor 126 or electrically connected to the processor 126.

In some implementations, the server 130 may be implemented as multiple servers and various components of the server 130 may be distributed across the multiple servers. Server 130 may be connected to computing device 120 through one or more networks. One or more operations of the method depicted in FIGS. 5, 7A, and 7B may be implemented in the computing device 120 or server 130 such that portions of the method may be executed by computing device 120 and other portions by server 130.

Server 130 may include any suitable computing device coupled to the one or more networks, including but not limited to a personal computer, a server computer, a series of server computers, a mini computer, and a mainframe computer, or combinations thereof. For example, server 130 may include a web server, or a series of servers, running a network operating system. In some implementations, the server 130 may be connected to or may be integrated with one or more databases, such as a fish profile database that stores profiles of fish.

Server 130 may also implement common and standard protocols and libraries, such as the Secure Sockets Layer (SSL) protected file transfer protocol, the Secure Shell File Transfer Protocol (SFTP)-based key management, and the NaCl encryption library. Server 130 may be used for and/or provide cloud and/or network computing. Although not shown in the figures, the server 130 may have connections to external systems providing messaging functionality such as e-mail, SMS messaging, text messaging, and other functionalities, such as encryption/decryption services, cyber alerts, etc.

The one or more networks may provide network access, data transport, and other services to the server 130. The one or more networks may include and implement any commonly defined network architectures including those defined by standards bodies, such as the Global System for Mobile communication (GSM) Association, the Internet Engineering Task Force (IETF), and the Worldwide Interoperability for Microwave Access (WiMAX) forum. For example, the one or more networks may implement one or more of a GSM architecture, a General Packet Radio Service (GPRS) architecture, and a Universal Mobile Telecommunications System (UMTS) architecture. The one or more networks may implement a WiMAX architecture defined by the WiMAX forum or a Wireless Fidelity (WiFi) architecture. The one or more networks may include, for instance, a local area network (LAN), a wide area network (WAN), the Internet, a virtual LAN (VLAN), an enterprise LAN, a layer 3 virtual private network (VPN), an enterprise IP network, corporate network, or any combination thereof. In some implementations, the one or more networks may include a cloud system that provides Internet connectivity and other network-related functions.

Server 130 may be connected to or may be integrated with one or more databases, such as a fish profile database. The one or more databases may include a cloud database or a database managed by a database management system (DBMS). A DBMS may be implemented as an engine that controls organization, storage, management, and retrieval of data in a database. DBMSs frequently provide the ability to query, backup and replicate, enforce rules, provide security, do computation, perform change and access logging, and automate optimization. Examples of DBMSs include Oracle® database, IBM® DB2, Adaptive Server Enterprise, FileMaker®, Microsoft® Access®, Microsoft® Structured Query Language (SQL) Server, MySQL™ PostgreSQL®, MongoDB, Mondo/ES JavaScript Object Notification (JSON), and a NoSQL implementation. A DBMS typically includes a modeling language, data structure, database query language, and transaction mechanism. The modeling language may be used to define the schema of each database in the DBMS, according to the database model, which may include a hierarchical model, network model, relational model, object model, or some other applicable known or convenient organization. Data structures can include fields, records, files, objects, and any other applicable known or convenient structures for storing data. A DBMS may also include metadata about the data that is stored.

Referring to FIGS. 2A-2F, in some implementations, the net pen system 210 may include different types of water, e.g., fresh water, salt water, water at different salinity levels, and may include one or more species of fish. The net pen system 210 may be made of any suitable material, such as glass, concrete, acrylic, plastic, or combinations thereof. Additional devices such as air pumps, water pumps, lighting systems, heating and cooling systems, and filtering systems may be used to regulate conditions in the net pen system 210.

Figure 2A:
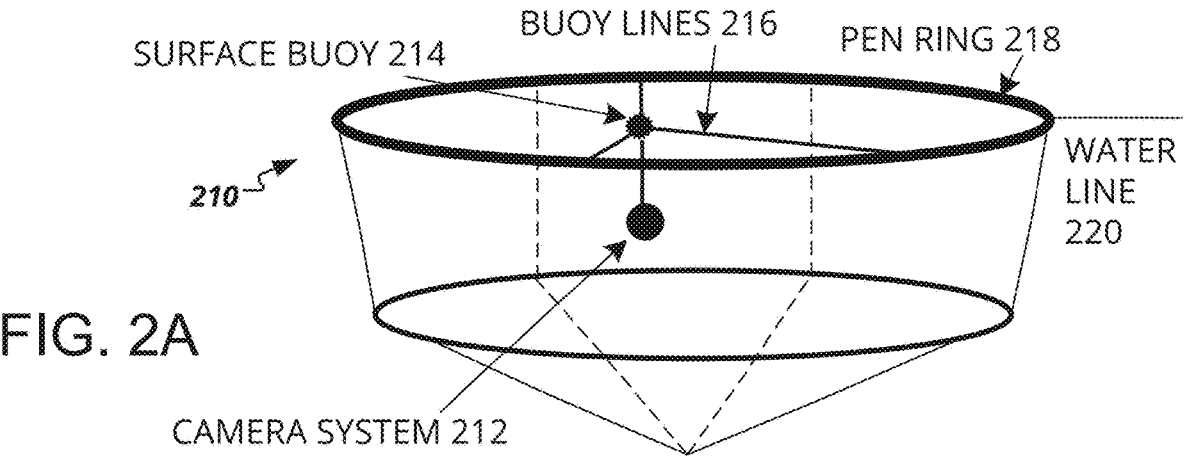
FIGS. 2A-2F depicts various implementations of a net pen system.

As shown in FIG. 2A, a net pen system 210 may include a cone-shaped base with a cylindrical structure extending from the cone-shaped base to a pen ring 218 that is positioned at the water line 220, which may be level with a top surface of water in the net pen system 210. In general, various configurations of a net pen system 210 may be used. For example, although the net pen system 210 is shown as having a cone and cylindrical structure, other shapes and sizes, such as rectangular, triangular, pyramid, or cubic shapes, may also be used.

A network of buoy lines 216 and cables may be dispersed through the net pen system 210. The network of buoy lines 216 and cables may extend from various parts of the net pen system 210, such as the pen ring 218, to a surface buoy 214 floating at the water line 220. A camera system 212 may be suspended from the surface buoy 214, which may be located at an intersection point of two or more of the buoy lines 216. The position of the surface buoy 214 can be adjusted by reconfiguring the buoy lines 216. For example, the buoy lines 216 may intersect each other at a center of the pen ring 218 or towards a side of the pen ring 218 and net pen system 210. The camera system 212 may then be positioned below the water line 220 and surface buoy 214, and towards the center or a sidewall of the net pen system 210.

The surface buoy 214 may be made of various suitable materials including, but not limited to, polyethylene elastomer or foam, polyurethane elastomer or foam, co-polymer foam, and syntactic foam. The buoy lines 216 and cables may be made of one or more suitable materials including, but not limited to, polypropylene rope, nylon rope, manila rope, Kevlar, and optical fibers. Other configurations and variations of the net pen system 210 are depicted in FIGS. 2B-2F.

Figure 2B:
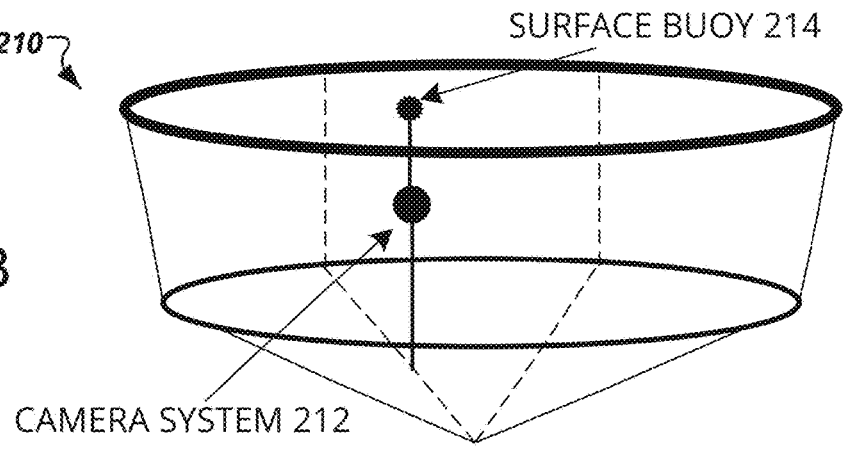

For example, as shown in FIG. 2B, in addition to the structure depicted in FIG. 2A, a cable may extend from the floor of the net pen system 210 to the camera system 212. The cable provides additional support for maintaining the position of the camera system 212, and reduces affects that surface waves and other surface interferences may have on the position of the camera system 212.

Figure 2C:
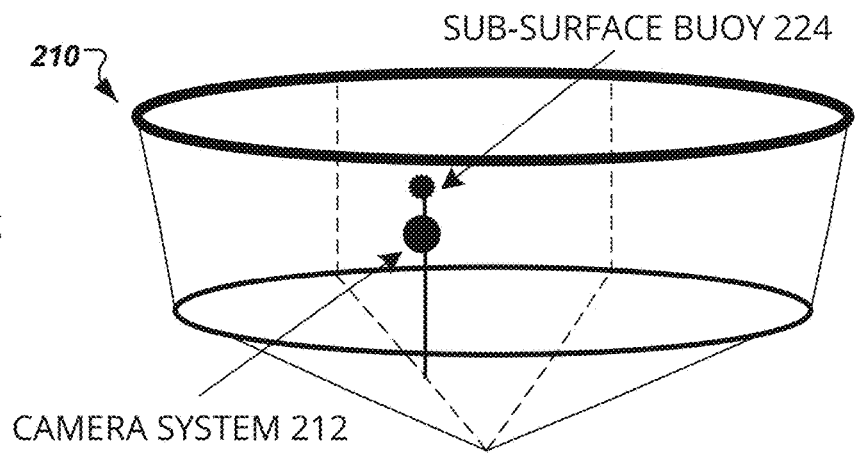

In some implementations, as shown in FIG. 2C, a sub-surface buoy 214 rather than a surface buoy may be utilized in addition to the cable extending from the floor of the net pen system 210. The sub-surface buoy 214 may have a different buoyancy level compared to a buoyancy level of a surface buoy, thus enabling the sub-surface buoy 214 to float at a depth in the water that is not at the water line 220. The cable connecting the sub-surface buoy 214 to the base of the net pen system 210 may extend from any portion of the base of the net pen system 210, and may be connected to the camera system 212 and sub-surface buoy 214. The camera system 212 may be positioned between the sub-surface buoy 214 and the base of the net pen system 210.

Figure 2D:
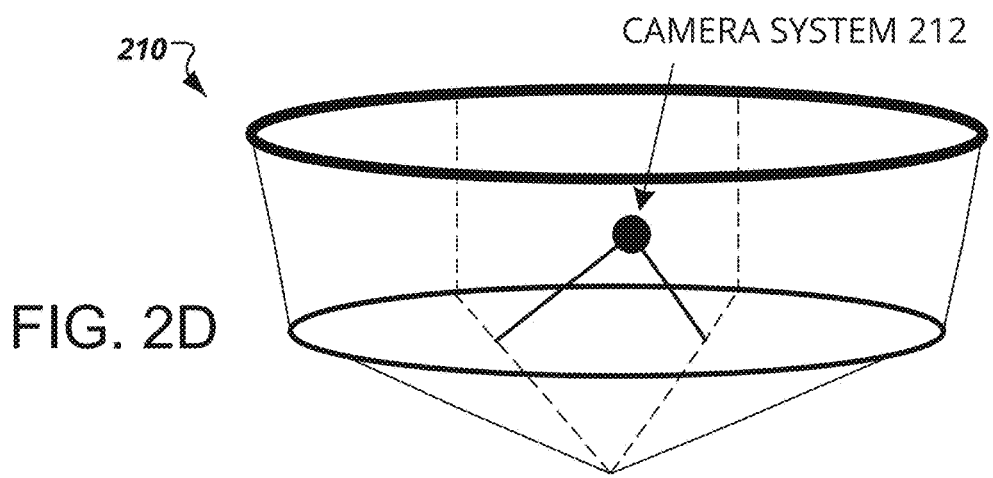
Figure 2E:
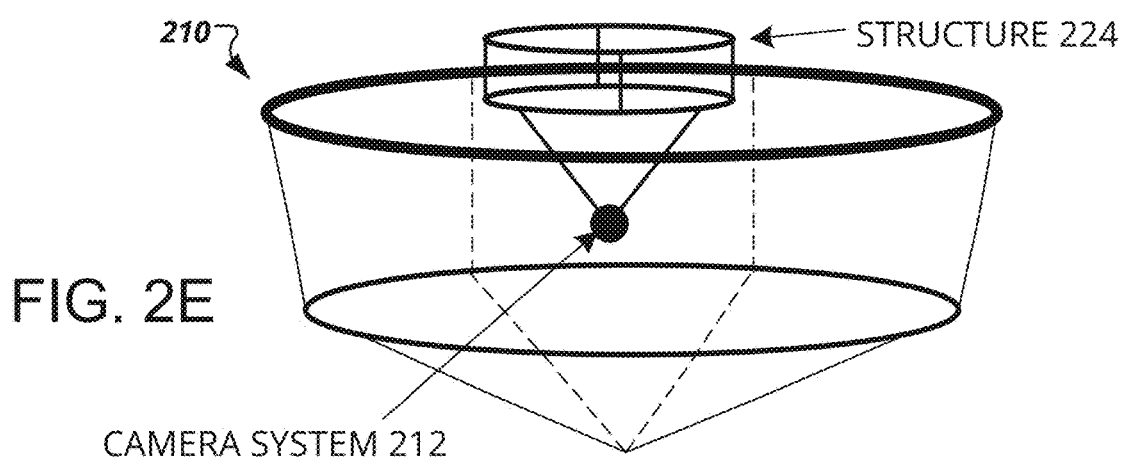
Figure 2F:
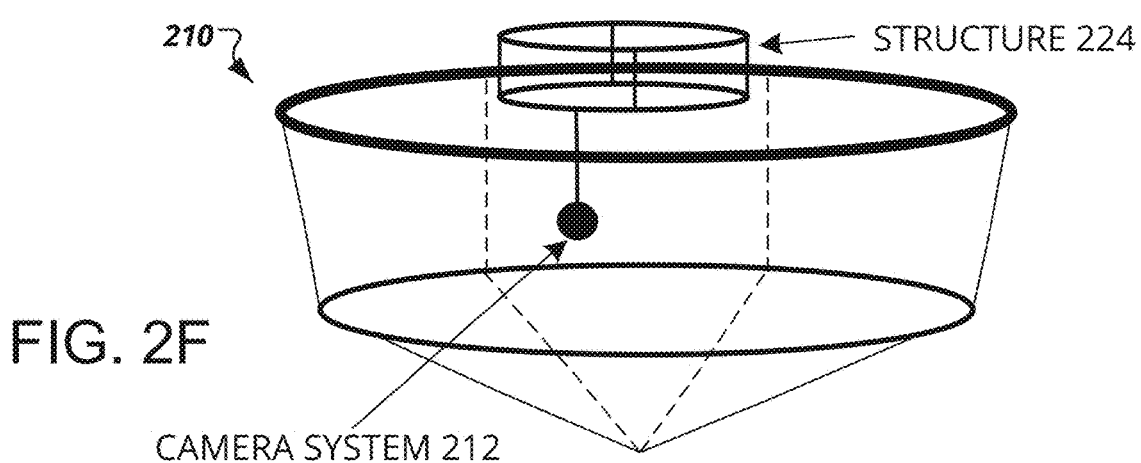

In some implementations, surface or sub-surface buoys may not be utilized. For example, as shown in FIG. 2D, two or more cables extending from the base of the net pen system 210 may be used to hold the camera system 212 in place. In the implementations shown in FIGS. 2E and 2F, a structure 224 may be deployed above the net pen system 210. The structure 224 may be made of various suitable materials, e.g., steel, metal, plastic, and may have various shapes and sizes. The structure 224 may be connected to one or more cables attached to the camera system 212, such that the camera system 212 is suspended from the structure 224 below the water line 220, even though the structure 224 may be completely or partially positioned above the water line 220. In the implementation of FIG. 2E, two cables extend from structure 224 to fix the position of the camera system 212. In FIG. 2F, a single cable extends from structure 224 to fix the position of the camera system 212.

In some implementations, the structure 224 may include rails, receiving plates, and locking mechanisms, and may be connected to a computer system. A locking mechanism may connect the one or more cables to structure 224. The locking mechanism may include a clamp, soldered joint, or any other material or apparatus to connect the one or more cables to the structure 224. The locking mechanism may be affixed to a receiving plate that can move along a rail attached to the structure 224. The receiving plate may move vertically or horizontally along portions of the structure 224 using the rail. The movement of the receiving plate cause the locking mechanism and cable connected to the received plate to move such that the position of the camera system 212 in the net pen system 210 is also adjusted.

For example, if a receiving plate moves horizontally by a certain distance, the camera system 212 also moves horizontally by the same distance and in the same direction. If the receiving plate moves vertically a certain distance, the camera system 212 also moves vertically by the same distance. In general, the receiving plate may be moved horizontally and vertically so that the camera system 212 may be positioned approximately parallel to a fish or such that at least one side of a body of the fish proximate to the camera system 212 is completely visible in a lens of the camera system 212. The camera system 212 may be moved manually or in response to receiving an electronic control signal from the computer system.

In some instances, two or more locking mechanisms may be controlled to move sequentially or simultaneously in the same direction and distance. In this manner, the camera system 212 may be dynamically positioned at various parts of the net pen system 210 in response to commands received from a computer system.

FIGS. 3A and 3B depict aerial views of a net pen system 310 with a fish monitoring system. The fish monitoring system may include multiple devices, filters, and sensors such as light sensors, thermometers, salinity sensors, and image acquisition systems. The image acquisition systems may include a camera system 312 with one or more cameras configured to obtain images and videos of fish in the net pen system 310.

As described above, the camera system 312 may be connected to a computer system located outside the net pen system 310. The computer system may control multiple parameters of the cameras such as position, lens focal length, or zoom, and may control the camera system 312 to obtain still or moving images of fish. The camera system 312 may include one or more motors configured to maneuver cameras in particular directions based on instructions received from the computer system. The computer system may receive the images from the camera system 312 for further processing.

The camera system 312 may be deployed in different locations within a net pen system 310. In general, the camera system 312 may be located at a position in the net pen system 310 that enables images of good quality, e.g., clear images of fish without blurriness, and an image of at least one complete side of the fish, to be captured by the camera system 312. For example, as illustrated in FIGS. 3A and 3B, the camera system 312 may be located in a relatively off-center location of the net pen system 310. This position may be utilized when fish are swimming in a school in a circular swimming pattern, as depicted in FIG. 3B. The camera system 312 may be held in position in various ways such as by using a surface buoy, sub-surface buoys, fixed structures, or cable lines, as described above.

Various factors may determine the position of the camera system 312 in the net pen system 310. For instance, in some cases, if fish in the net pen system 310 are the type of fish that swim against the current, the camera system 312 may be positioned substantially parallel to the current so that the cameras may have a relatively perpendicular angle with respect to the fish's body, as depicted in FIG. 3A. Other fish may swim with the current or may not have swimming patterns that are dependent upon a current. Some fish may swim in a circular pattern, as depicted in FIG. 3B. In some cases, the particular species of fish in the net pen system 310 may swim at particular depths or areas that have particular temperatures or amounts of light, and the camera system 312 may be positioned within the net pen system 310 to enable cameras 312A and 312B to focus on fish in these particular depths or areas. In view of these various factors that determine the likely location and swimming patterns of a fish, the position of camera system 312 may be determined and adjusted accordingly.

Referring now to FIGS. 3A-4E, a camera system 312/412 in a net pen system 310 may include multiple cameras. In some cases, cameras may be positioned in a horizontal arrangement, such as a left stereo camera 312A and a right stereo camera 312B. In some cases, cameras may be positioned in a vertical arrangement, such as an upper camera or a lower camera. In general, various configurations of the cameras may be used. Each of the cameras 312A and 312B may be installed in camera ports 408 and maybe positioned to obtain images and videos of fish in the net pen system 310. As noted above, under certain circumstances, the cameras 312A and 312B may be positioned to obtain images of fish at approximately perpendicular angles relative to the body of a fish so that a lateral view of one or more fish may be obtained.

Figure 4A:
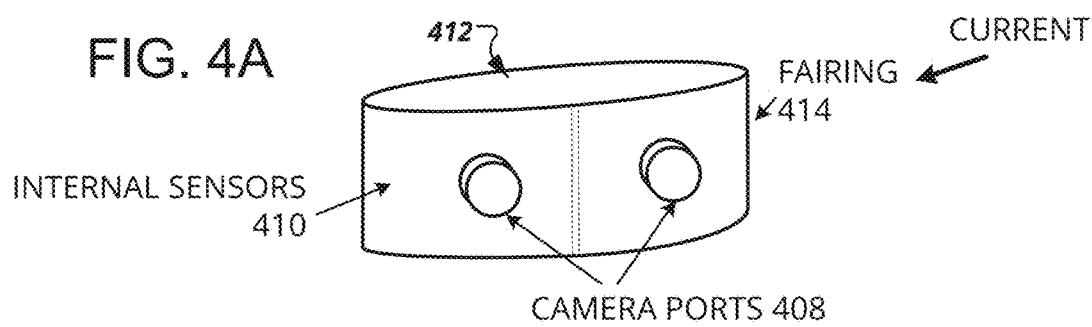
FIGS. 4A-4E depict various implementations of a camera system.

Referring to FIG. 4A, the camera system 412 may include internal sensors 410 to detect the direction of the current. Based on the detected current direction, the camera system 412 may adjust its position relative to the current direction so that a longitudinal axis of the camera system 412 is parallel to the current direction. The camera system 412 may include a fairing 414 that facilitates the movement of the camera system 412, for example, by reducing drag.

Figure 4B:
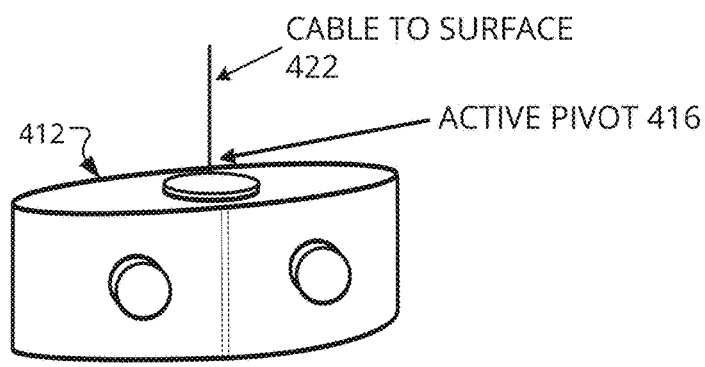

As shown in FIG. 4B, the camera system 412 may include an active pivot 416 that is a mechanical device configured to rotate the camera system 412 at any angle between 0° to 359°. The active pivot 416 may rotate the camera system 412 along a central axis running through the center of the camera system 412 from a top surface of the camera system 412 to a bottom surface of the camera system 412. The imaginary central axis may be collinear to a longitudinal axis of a cable line 422 attached to the camera system 412.

In some implementations, the camera system 412 may include a microcontroller that is connected to the internal sensors 410 and the active pivot 416. The microcontroller may provide instructions to the active pivot 416 to rotate according to the current direction detected by the internal sensors 410. For example, the microcontroller may determine that the camera system 412 should rotate by 26° counter clockwise, so that the camera system 412 is parallel to the detected current direction. The microcontroller may then send instructions to the active pivot 416 to rotate by 26° counter clockwise, and the active pivot 416 may adjust the position of the camera system 412 accordingly.

Figure 4C:
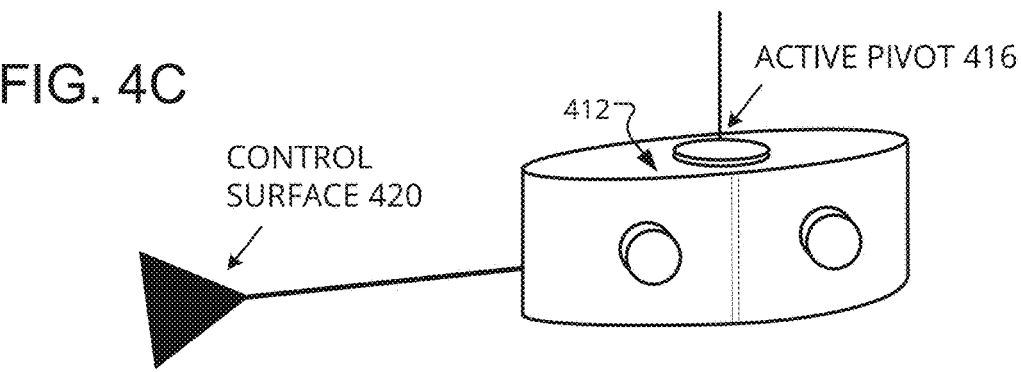

In some implementations, as shown in FIG. 4C, a control surface 420 may be attached to the camera system 412. The control surface 420 may have a flat triangular body attached to an elongated connector that is attached to the camera system 412. The control surface 420 may be active or passive. For instance, the flat surface of the control surface 420 may passively align itself along the current direction using the natural force of the water current. The elongated connector and active pivot 416 enable the camera system 412 to passively align itself with the control surface 420 and, consequently, the current direction.

In some implementations, the control surface 420 may be controlled by the microcontroller in the camera system. The microcontroller may utilize the control surface 420 and the active pivot 416 to move the camera system 412 in a particular direction. Thus, the control surface 420 may be utilized in a passive or active manner. Although the control surface 420 is described as having a flat triangular body attached to an elongated connector, in general, the control surface 420 may be implemented in several suitable shapes and sizes. For example, a rectangular or square flat surface may be used instead of a triangular flat surface, and various suitable types of connectors may be utilized.

Figure 4D:
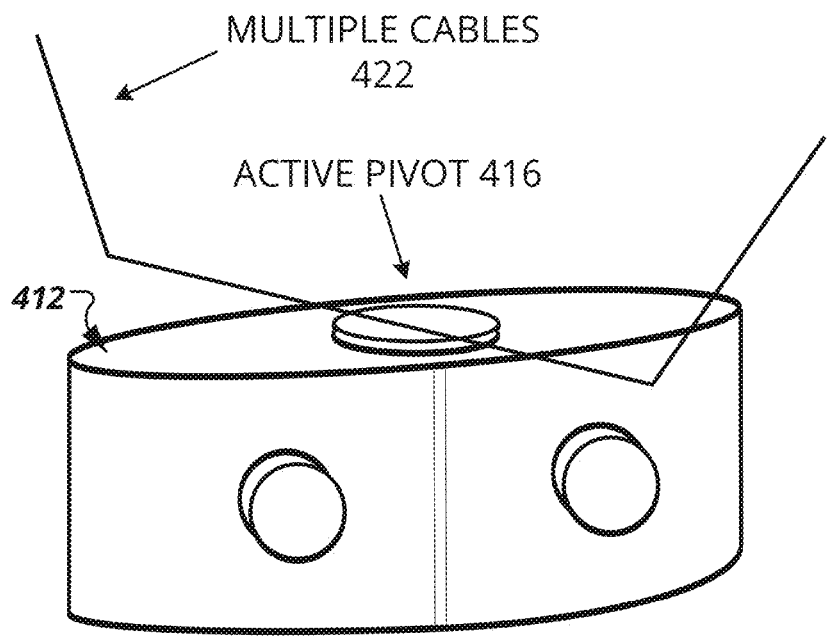
Figure 4E:
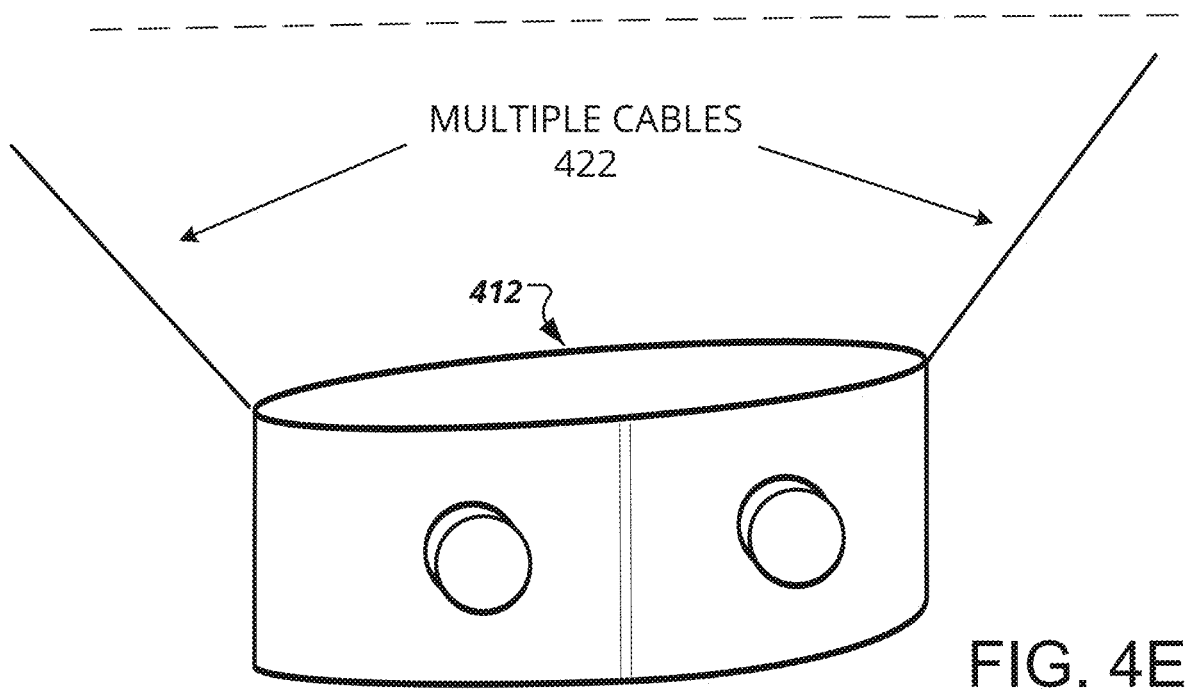

FIGS. 4B, 4D, and 4E depict different ways to connect the camera system 412 to cables and or buoy lines. For example, when a single cable line 422 is connected to the camera system 412, as shown in FIG. 4B, the cable line 422 may be attached to the active pivot 416 that rests on a surface of the camera system 412. The cable line 422 may be connected a top, bottom, or side surface of the camera system 412 depending on whether the cable line is connected to devices above, below, or to the side of the camera system 412. For instance, as shown in FIG. 4B, the cable line 422 is connected to a top surface of the camera system 412 since the cable line 422 extends to a device on the water line such as a surface buoy. In some cases, the cable line 422 may be connected to a bottom surface of the camera system 412 if the cable line 422 extends to the base or floor of the net pen system, for example, as shown in FIGS. 2B-2D.

When multiple cable lines 422 are connected to the camera system 412, each of the multiple cable lines may be affixed to the active pivot 416, as shown in FIG. 4D. This configuration allows the camera system 412 to rotate in any direction without disturbing the connection to the multiple cables. In some implementations, if an active pivot 416 is not integrated with the camera system 412, the multiple cable lines 422 may be attached to different parts of the camera system 412. For example, if two cables 422 extending to the water line are holding the camera system 412 in position, the two cables 422 may be attached to the camera system 412 on opposite ends of the top surface of the camera system 412.

As described above, various configurations of the camera system 312/412 may be utilized. The multiple cameras 312A and 312B may provide more than one image for a particular fish from slightly different angles. The multiple images may be used to improve characterization of the fish as described below with respect to FIGS. 7A and 7B.

In some implementations, the cameras 312A and 312B in the camera system 312 are calibrated before obtaining fish images. To calibrate the cameras 312A and 312B, the cameras 312A and 312B may capture images of reference patterns at different angles and distances relative to the camera lens, and a room mean square (RMS) error may be calculated by determining the difference between the captured images of the patterns and the reference patterns. If the RMS error satisfies an error threshold, settings of the cameras 312A and 312B may be adjusted to recalibrate the cameras 312A and 312B. Adjusting the settings of the cameras 312A and 312B may include any operation that modifies a captured reference image. The operations may include, but are not limited to, one or more of adjusting a position of a camera, adjusting a lens position of the cameras 312A and 312B, and adjusting an amount of zoom of the cameras 312A and 312B.

After adjusting the settings of the cameras 312A and 312B, another set of images may be captured and a second RMS error may be calculated. The calibration process may be repeated until the RMS error no longer satisfies the error threshold.

Figure 5:
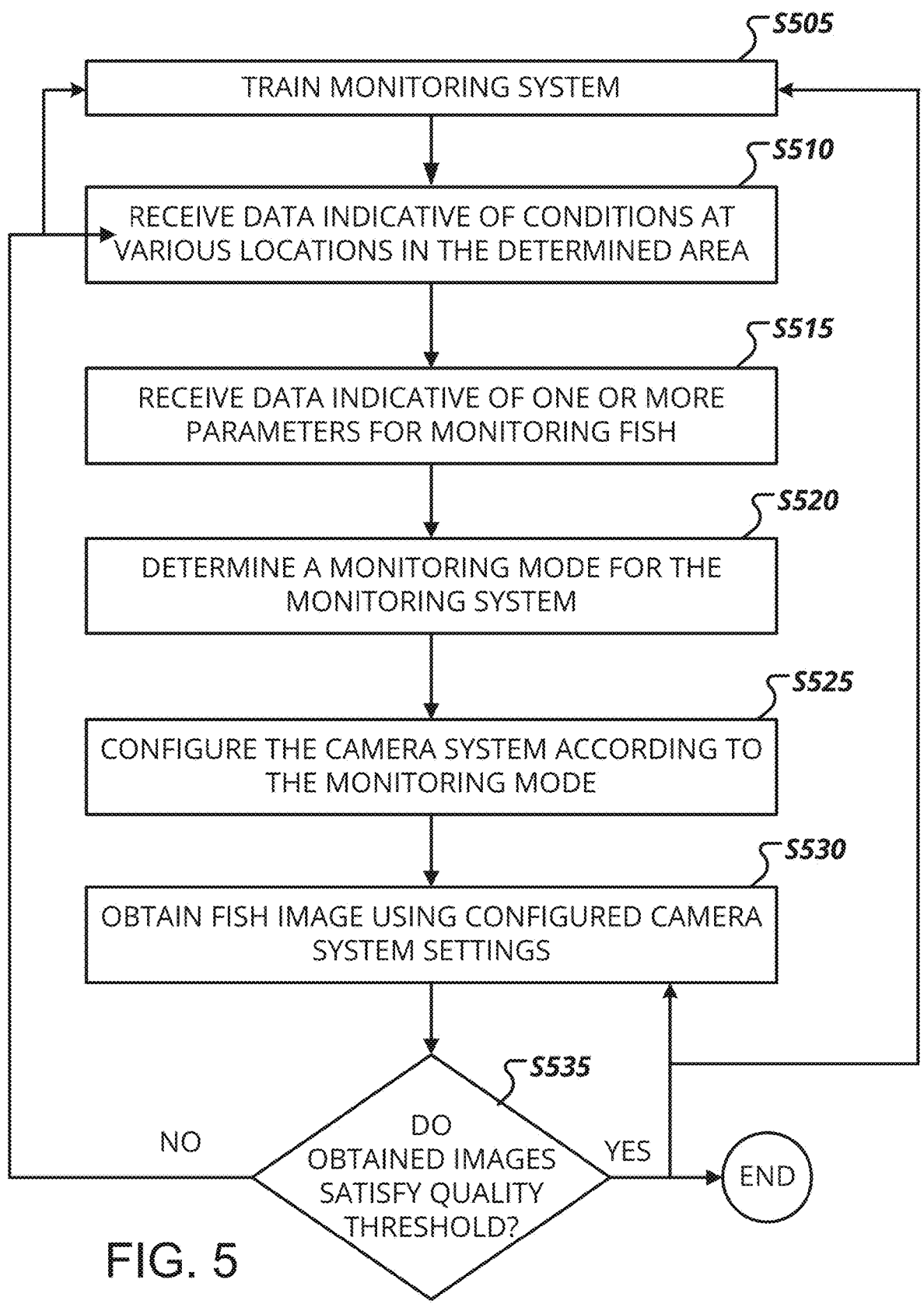
FIG. 5 depicts a flow chart of a method for configuring the fish monitoring system.

FIG. 5 depicts a flow chart of a method for configuring a fish monitoring system in a determined area such as a net pen system. The monitoring system may correspond to the system 100 described with respect to FIG. 1. One or more components of the monitoring system, such as the camera system controller and processor, may be periodically trained to improve the performance and reliability of the monitoring system (S505). Neural networks, machine-learning methods, and classifiers may be integrated into and utilized by the camera system controller and processor to train the monitoring system in various ways.

In some implementations, a system administrator may provide images as training data. In some cases, images previously obtained by one or more camera systems in the monitoring system may be used as training image data. The training images may include various images of fish with variations, and may be provided with tags or labels that identify the fish and features of the fish. Contextual training data indicating one or more of lighting conditions, temperature conditions, camera locations, topology of the determined area, current direction or strength, salinity levels, oxygen levels, fish activities, and timing data at the time an image was captured may also be provided with the training images.

Machine-learning techniques may be used to determine various relationships between the training image and the contextual training data. For example, the monitoring system may determine locations and depths that fish frequently feed in, the current conditions in which fish prefer to swim in, lighting, temperature, or salinity levels at which fish engage in certain activities, e.g., sleeping, eating, schooling. The monitoring system may also determine timings at which fish engage in certain activities. For example, if fish most frequently eat between 7-7:25 p.m. in a particular region of the determined area, the monitoring system may determine the 7-7:25 p.m. time block as one in which fish frequently feed in and the particular region as the location at which fish frequently feed.

The monitoring system may also learn preferred camera positions and locations based on the training data. For example, using the training images and contextual training data, the monitoring system may learn which cameras at particular locations and depths may be used to capture certain types of high-quality images. The monitoring system may also learn how to position cameras at certain locations and the camera settings that may be utilized to obtain quality images of fish. For instance, if a camera positioned at a 4° angle captures fewer images of fish or images of fish that do not capture an entire body of a fish but the camera positioned at an 84° angle captures more images of fish or images of fish that capture an entire body of a fish, the monitoring system may determine that the camera should be positioned at 84° to obtain images of fish.

As another example, the monitoring system may determine that a first type of fish most frequently swim at a depth of five meters in a circular pattern around the determined area, and that a second type of fish most frequently cluster feed at a northwest quadrant of the determined area between 7-7:25 p.m. The monitoring system may then identify cameras A, B, and C that are located within a threshold height difference from the depth of five meters, and use these cameras to obtain images of the first type of fish swimming.

Other cameras in the camera system that do not satisfy the threshold height difference may be configured to be deactivated for the purposes of imaging the first type of fish swimming. The threshold height difference may be set by an administrator of the monitoring system and may vary at different depths.

The monitoring system may also identify cameras F, H, and K located in the northwest quadrant of the determined area, and activate them daily between 7-7:25 p.m to obtain images of the second type of fish feeding. Cameras other than cameras F, H, and K may be configured to be deactivated for the purposes of imaging the second type of fish eating. If the location of a source of the fish food may be learned or provided to the monitoring system, for example, in instances in which a fish feeding device at a fixed location in the northwest quadrant is utilized to release fish food at particular times, the monitoring system may further control cameras F, H, and K to point towards the fish feeding device at the feeding times. The camera direction may be controlled by rotating a camera using an active pivot, as described with respect to FIG. 4B and 4D, or moving a camera to face a particular direction, for example, as described with respect to FIGS. 2E and 2F.

In some implementations if label or tag data is not included in the training images, classifiers may be used to classify the type of fish depicted in each image, the location of each fish in image, present or missing features of each fish in an image. For example, faster recurrent convolutional neural network (RCNN) may be utilized to detect a fish in an image and its location in the image. One or more of semantic segmentation, DeepPose operations, and convolutional neural networks may be used to determine features of a fish in an image.

Classifiers may also determine the angle of a fish's body relative to a camera from the body position of a fish in an image, and a type of activity that the fish is likely engaged in an image. With the use of neural networks, machine-learning methods, and classifiers, the monitoring system may be trained to learn or identify the type of fish in an image, the features, e.g., fins, tails, and properties, e.g., shape, size, color, of the features of a fish detected in an image, a location of a fish in an image, camera positions and viewing angles of a fish captured in an image, and one or more conditions, such as location, determined area topology, timing, lighting, depth, salinity, current, temperature, associated with one or more activities that fish are engaged in.

Based on the training, the monitoring system may determine monitoring modes of operation for its camera system that includes multiple cameras. Each monitoring mode may have an associated set of conditions and parameters, as shown below in TABLE I.

TABLE I

| Mode | A | B | C | D | E | F |
|---|---|---|---|---|---|---|
| Fish Type | Atlantic Salmon | Atlantic Salmon | Pink Salmon | Rainbow Trout | Pacific Halibut | Pacific Halibut |
| Activity | Schooling | Eating | Swimming | Sleeping | Swimming in position | Eating |
| Time | 7-7:40 a.m.; 5:15-5:50 p.m. | 6:20 a.m.-7:20 a.m. | n/a | 2-3:30 a.m. | n/a | 8-8:50 a.m.; 1:15-1:45 p.m. |
| Location | (x, 2 to 20, x) | (15, 3, 41) | (x, x, x) | (x, 10 to 20, −10 to −40) | (55, −2, 2) | (74, 1, 8) and (−10, 35, −23) |
| Cameras | A, C, E | C | A-G | B, F | G | D, H |
| Conditions | Against current, 8,000-10,000 lux | Against n/a | | 50°-54° F., current, 34 ppt | 34 ppt | 100-400 lux |

As shown in TABLE I, the monitoring system may have multiple monitoring modes. The monitoring modes may be for the same type of fish, e.g., two modes for the Atlantic salmon, or different type of fish, e.g., pink salmon and rainbow trout. The modes may have learned values for certain parameters and conditions, such as the activity, time of activity, location of activity, cameras that can be used to obtain images of the activity, and conditions associated with the activity such as timing, lighting, depth, salinity, current, temperature. The values, camera, and fish identifiers listed in TABLE I are for exemplary and illustrative purposes. Various configurations of monitoring modes for various fish may be learned and determined by the monitoring system.

Although not shown in TABLE I, when a particular camera is associated with a mode, camera settings, such as one or more of camera location, rotation angle for the active pivot, lens focus, and zoom, for the particular camera are also stored. Location information may be provided based on a coordinate system used to map the determined area. A 3D coordinate system using Cartesian coordinates or cylindrical coordinates may be used. In some implementations, Global Positioning System (GPS) coordinates may be used and may specify latitude or longitude information.

As an example, a mode A may indicate that the images of the Atlantic salmon engaged in schooling may be obtained using cameras A, C, and E. Respective settings for cameras A, C, and E may also be stored for mode A. The Atlantic salmon may typically engage in schooling between 7-7:40 a.m. and 5:15-5:50 p.m when swimming against the current with light levels in the range of 8,000 to 10,000 lux. The schooling activity may occur at a particular depth corresponding to a range of two to twenty in one dimension of the 3D Cartesian coordinate system used to map the determined area. This range may correspond to, for example, a depth of one to eight meters in the determined area. An indicator, such as "x," may be used to denote all possible values. For example, the location coordinates for mode A are (x, 2 to 20, x), which indicate that schooling activity occurs at various x and z values of the coordinate system, but is between two to twenty in the y coordinates.

In some monitoring modes, there may not be sufficient information to provide values for a particular parameter or condition and the Table I may use an indicator, such as "n/a" as shown in TABLE I, to indicate that sufficient information is not available for the particular parameter or condition, e.g., the time parameter in modes C and E and the conditions for mode B. In some modes, one or more of the parameters or conditions may be optional or mandatory to execute the monitoring mode. For example, the condition of having salinity levels of 34 ppt to execute monitoring modes E and F may be optional. In some cases, for modes associated with swimming activities, the time parameter may be optional. For other modes, such as modes associated with feeding, the time parameter may be significant to execute the modes.

As described in the foregoing description, the monitoring system may be trained using neural networks, machine-learning methods, and classifiers, and may generate a dynamic list of monitoring modes based on the training (S510). The training may be a continuous process and the monitoring system may dynamically create or modify monitoring modes based on its training.

After the training, the monitoring system may be used to capture images of fish with minimal operator or human intervention. Using its network of sensors, the monitoring system may receive data indicative of one or more conditions at various locations in the determined area (S510). The data received from the sensors may include, but are not limited to, luminosity levels, temperature levels, salinity levels, oxygen levels, detected motions and motion types, current direction and magnitude, and one or more images. These sensors may be deployed at fixed or variable locations, and the data received from the sensors may also include parameter data such as time and location data (S515), so the monitor system may determine the types of conditions existing at different locations in the determined area.

In some implementations, data indicative of the conditions in the determined area may be provided by an administrator of the monitoring system. Thus, an administrator may use a computer system to input data to describe the conditions at one or more locations in the determined area. The ability for an administrator to input information allows the monitoring system to receive additional data that monitoring system devices, e.g., sensors, may not have detected, and, in some cases, may allow the administrator to correct data received also from malfunctioning devices in the monitoring system.

After receiving data indicative of the parameters and conditions in the determined area, the monitoring system may determine a monitoring mode for the camera system (S520). In some implementations, the monitoring system may determine the monitoring mode by determining whether the detected conditions and parameters match one or more monitoring modes. For example, if the monitoring system receives data from its sensors indicating that, at approximately 2 a.m., the temperature is in the range of 50°-54° F. and the luminosity levels are in the range 100-400 lux around a location of (55, −2, 2) in a net pen system that has pacific halibut, the monitoring system may determine that monitoring mode E, as shown in TABLE I, should be executed.

In general, if the match between the parameters and conditions detected by the monitoring system and the parameters and conditions associated with a stored monitoring mode satisfy a matching threshold, then the monitoring mode may be selected. For instance, if the matching threshold is set at 70%, then a monitoring mode may only be selected if the match between the parameters and conditions detected by the monitoring system and the parameters and conditions associated with a stored monitoring mode is greater than or equal to 70%.

In some implementations, one or more monitoring modes may be scored based on the amount the parameters and conditions detected by the monitoring system match the parameters and conditions associated with the one or more monitoring modes. The monitoring mode having the highest score among the scores for the one or more monitoring modes may be selected.

In some implementations, in addition to the threshold match, if a monitoring mode has a required condition or parameter, the required condition or parameter must also be satisfied. For example, if a monitoring mode, such as mode D in TABLE I, has a required luminosity condition of 100-400 lux, then mode D may not be selected unless the detected light levels at locations (x, 10 to 20, −10 to −40) correspond to 100-400 lux. In some implementations, certain parameters such as the fish type have to be satisfied for a monitoring mode to be selected.

In some implementations, the monitoring system may determine the monitoring mode in accordance with instructions received from an administrator of the monitoring system. The instructions received from the administrator may override or confirm matching monitoring modes determined by the monitoring system. For example, an administrator may submit instructions to the monitoring system at 7 a.m. to execute mode A, as shown in TABLE I, instead of mode B.

After determining the monitoring mode for the monitoring system, the monitoring system may configure the camera settings according to the determined monitoring mode (S525). For example, referring back to TABLE 1, if the monitoring system selects mode A, cameras A, C, and E in the camera system may be activated and configured according to the camera settings specified in mode A. The camera settings may specify a location of the camera, a tilt angle of the camera, a rotation angle to be used by an active pivot attached to the camera, zoom levels, and camera lens settings. The monitoring system may then send instructions to the microcontrollers in cameras A, C, and E, which execute the received instructions to configure the camera according to the camera settings stored for a particular mode. In some cases, if the camera has a variable location, the monitoring system may also send instructions to devices in the monitoring system, such as the rails and receiving plates described with reference to FIGS. 2E and 2F, to move the camera to a location specified by the determined monitoring mode.

In some implementations, when the monitoring system determines to use one or more monitoring modes, any cameras that are not configured to implement the determined monitoring modes may be deactivated. For instance, if the monitoring system determines that only monitoring modes B and F, as shown in TABLE I, are to be implemented for a 24 hour period, cameras C, D, and H may be configured according to the settings specified in monitoring modes B and F, and other cameras, such as cameras A, B, and E-G may be deactivated for the 24 hour period.

After configuring cameras in the camera system, the monitoring system may obtain images of fish according to the determined monitoring modes (S530). For instance, if monitoring modes B and D, as shown in TABLE I, are selected, camera C obtain images of fish between 6:20-7:20 a.m., and cameras B and F obtain images of fish between 2-3:30 a.m.

Images captured by the camera system may be transmitted through cables to a computer system, which may further process and analyze the images. In some implementations, the monitoring system may execute quality tests to determine if the obtained images satisfy a quality threshold or quality factor (S535). For example, the monitoring system may determine if the captured image is of the correct fish type or that the image quality is not significantly compromised by factors such as blurriness, partial or incomplete imaging of a fish, noise, insufficient light, and obstructions in the image of a fish.

In some cases, the quality factors may be assigned a weight and a net quality rating (NQR) for an image may be determined based on the factors and their respective weights. As an example, net quality rating may be calculated using the Equation 1.

$$NQR = (\text{Fish type})(W1) + (\text{blurriness})(W2) + (\text{complete fish image})(W3) + (\text{sufficient light})(W4) + (\text{lack of noise})(W5) + (\text{lack of image obstructions})(W6) \quad \text{Equation 1}$$

The weights, W1-W6, may be assigned different values. For example, in some cases, the fish type factor may have the highest weight, e.g., greater than 0.8. If the net quality rating NQR satisfies a quality threshold set by the administrator, the image may be stored and utilized for one or more applications, as described further below. The monitoring system may also instruct the activated cameras to obtain more images if the images received from the activated cameras are providing images that satisfy the quality threshold.

If the net quality rating NQR of an image fails to satisfy the quality threshold, the image may not be stored or utilized, and the monitoring system may return to operation S510 to detect conditions and parameters in the monitoring system. If there were any errors in identifying the conditions and parameters in the monitoring system, the errors may be rectified by repeating the process of receiving data indicating the conditions and parameters in the monitoring system. In addition, in some implementations, images that fail or pass the quality threshold may be used as training images to further train the monitoring system. The monitoring system may thereby continuously learn and adjust monitoring modes based on obtained images.

Images that pass the quality threshold may be used for one or more applications. For example, if a feeding device is used to feed fish and images obtained for a monitoring mode related to fish eating is being executed, the monitoring system or a monitoring system administrator may turn off the feeding device if no more fish are eating the food in obtained images. This prevents food waste and overeating of fish. In addition, an administrator may obtain real-time information of fish behavior in a part of the determined area, which may not otherwise be viewable by the administrator without the monitoring system.

As another example, by obtaining images of fish engaged in certain activities, researchers may be able to classify behavioral patterns and learn more about behaviors of fish when engaged in particular activities. Since the modes may be customized for particular activities, researchers do not have to filter through thousands of images to identify which images are pertinent to the activity they are researching. Rather, only relevant data is provided to the researchers.

As another example, by obtaining images of fish and identify features of the fish, as explained in further detail below with respect to FIGS. 7A, 7B, and 8, the monitoring system may allow a fish to be tracked, profiled, and provide information indicative of fish characteristics and behaviors, such as whether a fish is sick, behaving abnormally, eating, or not eating.

The ability to control and configure cameras to obtain images of fish can provide various advantages and may be used for numerous applications. Some advantages include being able to position cameras and configure camera settings based on machine-learning to obtain quality images of fish. Researchers and system administrators do not have to go through numerous unrelated or poor quality images of fish. Instead, the monitoring system can be configured to obtain pictures for certain types of fish and activities, and may filter out images that are not relevant or have poor quality.

In addition, since neural network and machine-learning functions are implemented by the monitoring system, the monitoring system may dynamically adjust monitoring modes by modifying or creating monitoring modes according to its training data. Since images obtained by the monitoring system are also used for training purposes, the monitoring system may be periodically or continuously updated in real-time. Human intervention or input may be minimized.

FIGS. 6A-6C depict exemplary implementations of the fish monitoring system operating in different modes. In FIGS. 6A-6C, a computer system 610 may communicate with camera system 620 located in a determined area. The camera system 620 may be attached to a cable and an active pivot 625, which may rotate the camera system 620 along the longitudinal axis of the cable. A fish-feeding device 630 may be located in close proximity to the camera system 620.

FIG. 6A depicts a scenario in which a monitoring mode for obtaining images of fish swimming against the current is being executed. The camera system 620 is configured according to the camera settings specified by the executed monitoring mode. The camera system 620 transmits images 640A of the fish through one or more cables connected to the camera system 620 and the computer system 610.

Camera system 620 is connected to motion sensors that detect motion that occurs within a radial distance of the camera system 620. The camera system 620 continues to send images 640A until the motion sensors detect motion within the radial distance of the camera system 620 or until the expiration of time period specified by the monitoring mode being executed. For example, as shown in FIG. 6B, the camera system 620 stops transmitting images 640A when no motion of fish is detected by the motion sensors or when the time period for taking pictures specified in the monitoring mode expires.

After some time, the camera system 620 may execute a second monitoring mode for obtaining images of fish feeding. In some implementations, the second monitoring mode may have an image acquisition timing that matches the timing of the release of food by the fish-feeding device 630 such that the fish-feeding device 630 releases fish food at the same time that the second monitoring mode commences. The active pivot 625 may then rotate camera system 620 by an angle according to the camera settings specified by the second monitoring mode.

In some implementations, the motion sensors in the camera system 620 may detect fish motion around the fish-feeding device 630 when the fish-feeding device 630 releases fish food. The microcontroller in the camera system 620 may receive data indicative of the direction or location of the motion from the motion sensors and determine a rotation angle for the camera system 620 to be directed towards the location at which motion has been detected. The microcontroller may then control the active pivot 625 to rotate the camera system 625 in the direction of the fish eating the fish food.

After being rotated, the camera system 620 obtains one or more images 640B of fish eating the fish food, and transmits the images 640B to the computer system 610 through one or more cables. The same camera system 620 may be redirected in different directions and configured according to different camera settings in different monitoring modes to capture images of fish engaged in different types of activity.

After positioning cameras in regions of interest in the determined areas, the monitoring system may perform additional processing on the images of fish. FIGS. 7A and 7B depict an exemplary flow diagram of a method for determining a size, shape, and weight of a fish. The method may be implemented by the system described further with reference to FIG. 1. The system may include cameras that are calibrated as described above and configured to obtain one or more images of fish in a net pen system (S705). The images may include a left stereo image 705A and a right stereo image 705B obtained from a left stereo camera and a right stereo camera, respectively.

The captured images 705A, 705B may be preprocessed (S710). The preprocessing may include image enhancement and rectification. For example, images 705A, 705B may be enhanced by performing one or more of histogram equalization, filtering, dehazing, deblurring, or denoising to improve image quality. In some cases, light levels may be boosted, for example, by merging multiple images obtained in a burst mode. In some cases, color in an image may be enhanced by performing adaptive histogram equalization.

In some cases, in response to capturing images 705A, 705B with poor image quality, the cameras may be recalibrated as described above. For example, a captured image 705A or 705B may be evaluated to determine a quality of the image or the depiction of a fish in the image. If the image 705A or 705B is significantly blurred, has occlusions, or the fish is at an undesired angle relative to the camera, e.g., a longitudinal axis of the fish is not perpendicular to the camera, the cameras may be recalibrated and another image may be captured.

In some implementations, as part of the preprocessing, an identification of a fish in an obtained image may be determined. For example, a fish that has been tagged or marked using methods such as, e.g., morphological marks, genetic marks, microtags, passive integrated transponder tags, wire tags, radio tags, may be identified by its tag or marker. In some implementations, obtained images may be examined to identify a unique spot pattern of a fish. This unique dot pattern may correspond to a signature of the fish and may be used to identify the fish in subsequent and previous images.

In some implementations, as part of the preprocessing, the left and right stereo images 705A and 705B may be combined to form a single image using any suitable image combination or merging technique such as stereo correspondence techniques. Object detection may be performed to detect fish in multiple, preprocessed images or the single, preprocessed image 710A (S710). In some implementations, faster recurrent convolutional neural network (RCNN) may be utilized to perform the object detection.

In some implementations, semantic segmentation may be performed to segment a fish in an image from the background in the image. Semantic segmentation may make it easier analyze detailed features of a fish. In general, various suitable object detection techniques may be used to detect fish in a single, preprocessed image 710A.

Figure 7A:
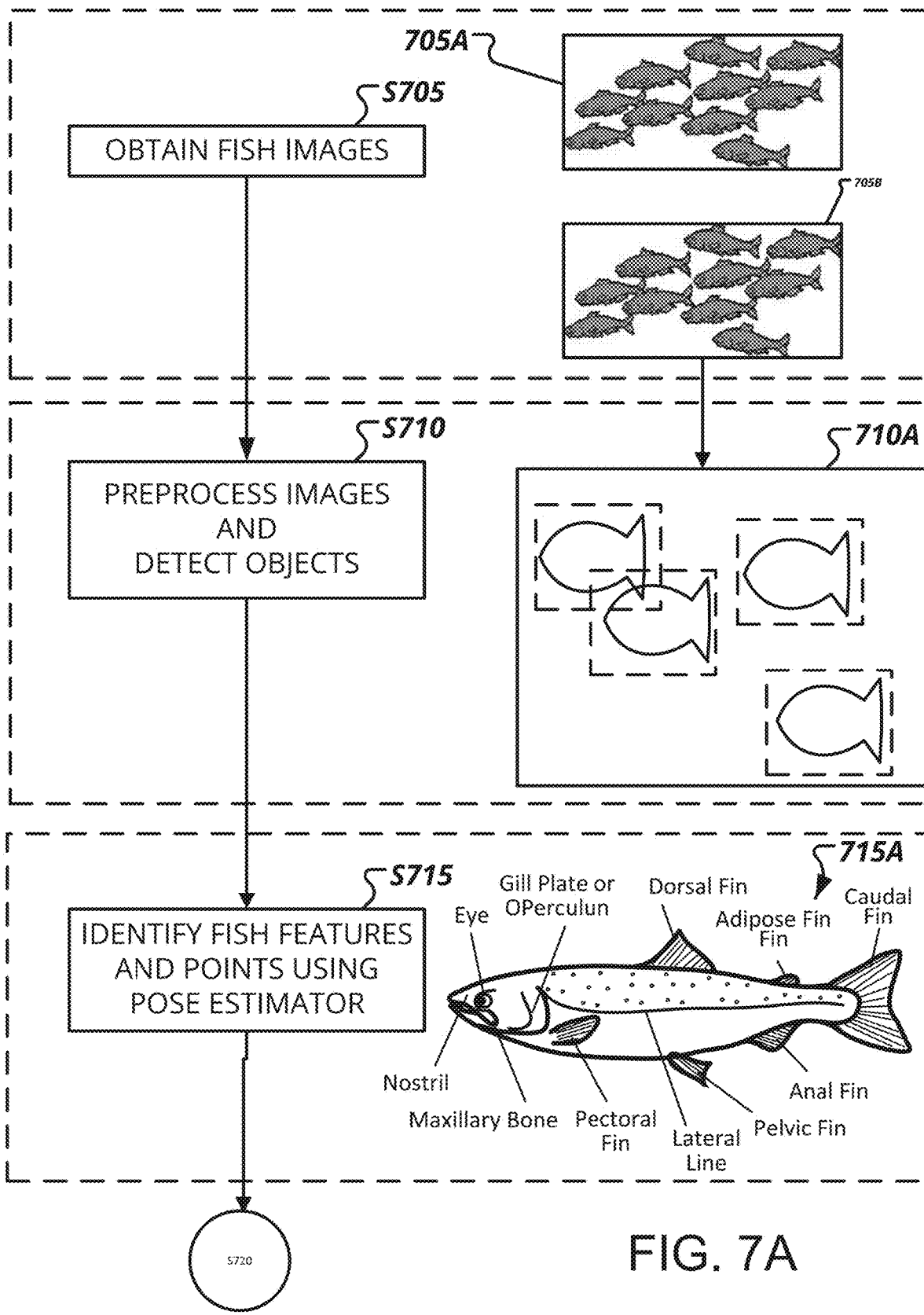
FIGS. 7A and 7B depict a flow chart of a method for determining fish, size, and weight.
Figure 7B:
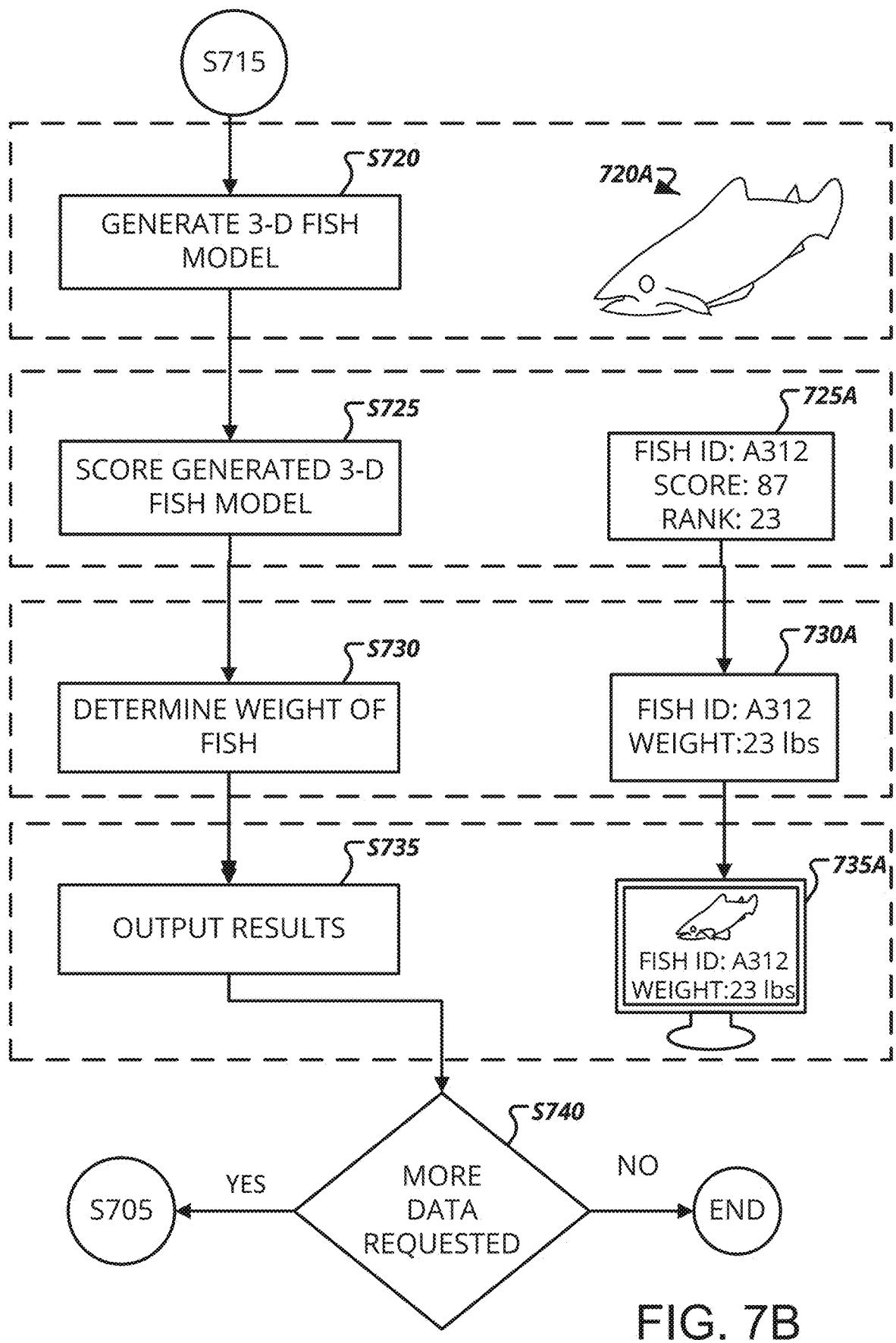
Figure 8:
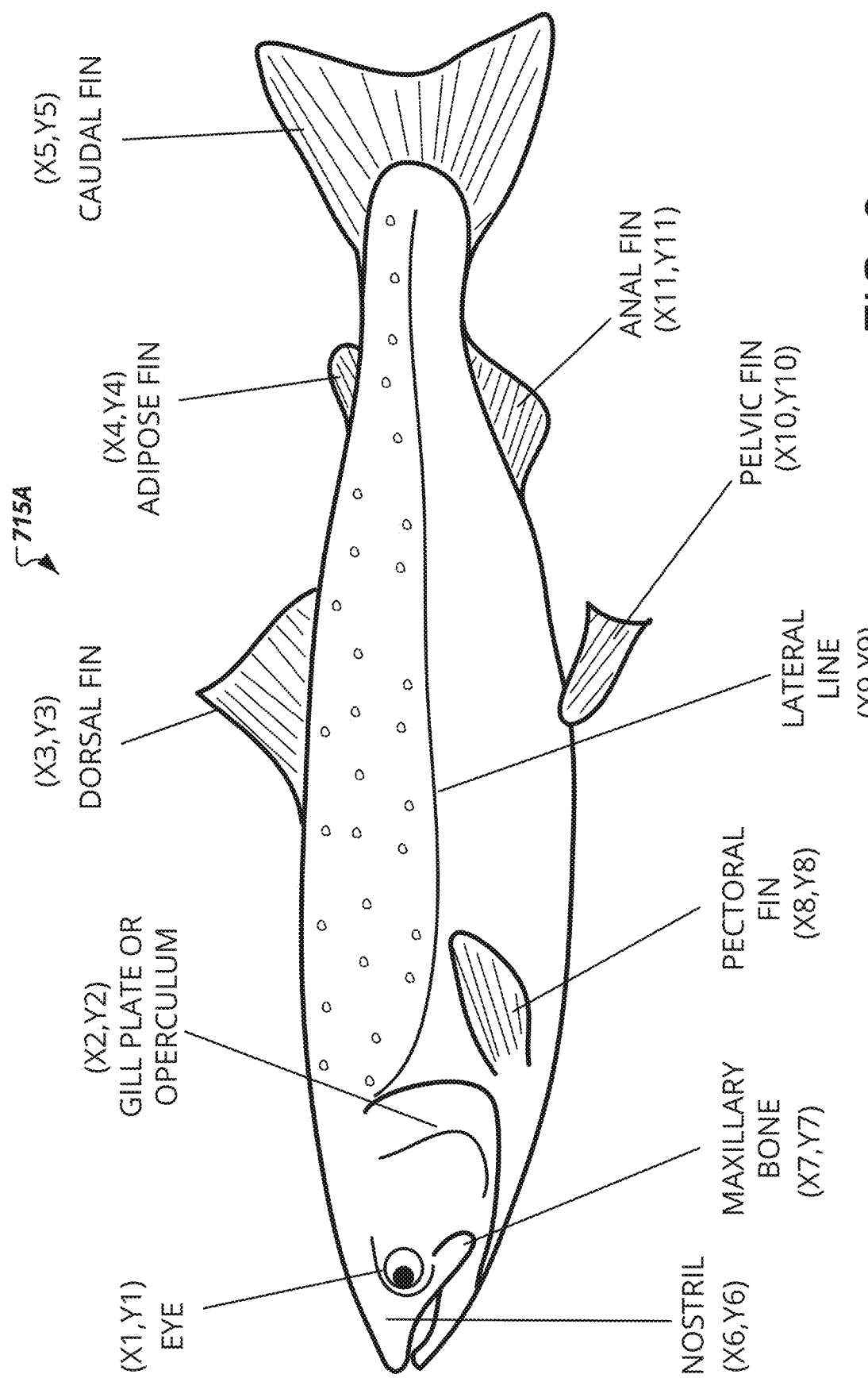
FIG. 8 depicts an image of an example fish with labels corresponding to features of the fish.

As shown in FIG. 7A, bounding boxes may be used to identify detected objects in an image 710A. The bounding boxes may include measured dimensions based on depth measurement and an indication of a margin of error in the measured dimensions. The bounding boxes or detected objects may correspond to regions of interest in the image 710A such as the images of fish in the image 710A. If multiple frames are being processed, a nearest neighbor algorithm may be used to find the most likely match of objects between frames.

In some implementations, a depth map may be generated to determine a distance of a fish from the camera. The depth map may be generated using any suitable technique. For example, Rayleigh scattering or image array depth reconstruction may be used to create a depth map. In addition, one or more of stereoscopic cameras, sonars, acoustic cameras, or lasers may be utilized to determine the distance of a fish from the camera lens.

After detecting a fish in one or more images, e.g., a combined single image, a stereo image pair, or a sequence of images, and using bounding boxes to identify regions of interest, a pose estimator may be used to identify key points in each region of interest (S715). In some implementations, the pose estimator may execute DeepPose operations, multi-fish pose estimation operations, or convolutional neural network operations. As shown in image 715A, an enlarged version of which is shown in FIG. 8, the key points may be associated with features of the fish such as an eye, nostril, gill plate, operculum, auxiliary bone, pectoral fin, lateral line, dorsal fin, adipose fin, pelvic fin, anal fin, and caudal fin. Key points may be labeled by numerical coordinates reflecting pixel positions in an image and may be associated with a particular feature of the fish.

In some implementations, when the key points and associated features may be partially occluded or non-viewable in an image, the pose estimator can still identify likely key points and associated features based on the probability of a key point and associated feature being present at a particular location. The probability of a key point location may be based on one or more of a likely shape, size, or type of the fish in the image or the location of other features of the fish. For example, using FIG. 8 as a reference, even though the adipose fin may not be shown in an image, the location of the adipose fin may be estimated using a probability model based on the position of the caudal fin and the dorsal fin in the image.

Next, a 3D model 720A of the fish may be generated using the identified key points associated with features of the fish (S720). In general, various 2-D to 3D conversion techniques may be used. For example, in some implementations, key points in the 2-D images may be mapped to a 3D model 720A of the fish using the depth map. The depth map may be determined using various techniques such as a block matching algorithm, depth from motion, or stereo processing by semi-global matching and mutual information. Objects, e.g., fish, in the stereo images, e.g., left and right images, may be detected, the depths from the cameras determined, and disparities between the images and detected objects may be used to generate the 3D model 720A. The 3D model 720A provides an estimated shape and size of the imaged fish.

In some implementations, the generated 3D model 720A may be scored and ranked. The score and rank reflects a quality factor of a generated 3D model and the captured image of a fish. The scoring of the model 720A may be determined based on a number of parameters including one or more of an elevation angle of a fish relative to the camera, a flatness level of the fish relative to the camera, a pose or perpendicularity of the fish relative to the camera, a distance of the fish relative to the camera, or neural network models for scoring particular poses. Values for the elevation angle, flatness level and perpendicularity of the fish and the distance of the fish from the camera may be determined in the previous operations such as when determining a depth map and determining the locations of key points. In some cases, the various parameters may be assigned different weights.

For example, in some cases, fish having higher elevation angles or fish at greater distances from the camera may have a lower score. In some cases, images of fish in which the fish does not appear relatively perpendicular or flat to the camera may be scored lower. In some cases, the number of determined key points may be used to calculate a score. For example, a higher score may be given to images for which a greater number of key points were determined from the image or fewer key points were determined using a probability model due to a lack of one or more key points being visible in the image. In general, the higher the score, the better the quality of the image and 3D model.

The score of the 3D model 720A may be ranked alongside other scores of 3D models for the same fish, if available (S725). For example, as shown in item 725A in FIG. 7B, the 3D model 720A of a fish assigned an identification, such as A312, has a score of 86 and is ranked 23. In general, various types of scoring systems and ranking systems using the criteria described above may be utilized.

If the score or ranking satisfies a threshold, the 3D model 720A may be utilized to determine a weight of the fish (S730). For example, if the threshold is a score of 85 or higher or a rank of 25 or higher, the 3D model 720A may satisfy the threshold based on the score and rank shown in item 725A. The threshold may be set differently for different fish, environments, or net pen systems.

To determine the weight of the fish, a linear regression model may be used to map the 3D model 720A to a weight. For example, the coordinates of key points in the 3D model 720A may be used to determine distances between two key points, and the determined distances and key points may be input into a linear regression model to determine an estimated weight of the fish. As shown in item 730A of FIG. 7B, the imaged fish having an ID of A312 may have an estimated weight of 23 lbs.

The estimated weight, shape, size, and 3D model of a fish captured in an image may then be output as results (S735). The results may be output in several manner. For example, in some cases, the 3D model 720A and the estimated weight, shape, and size may be displayed on the display 735A of a computer device. In some cases, the results may be stored in a fish profile for the fish in a database. The results may be added or aggregated to previous results associated with the fish. New average values for the weight and size dimensions may be determined periodically or each time new results are generated.

In some implementations, the stored fish data could provide a track record of the fish. For example, a fish could be tracked through its lifetime in a net pen system. A fish may be tracked from birth and through its growth to a fully developed adult fish. As such, details of the timing and type of changes a fish underwent may be recorded. If a party, such as a researcher or fish purchaser, is interested to learn more about a fish's history, the fish database may be queried to retrieve information about the fish's history.

In some implementations, the results may be provided to train the pose estimator. For example, an image of a fish and its determined 3D model, estimated weight, shape, and size may be provided as a reference to train the pose estimator as training data or to use as a weighted average for the overall fish weight computation. If feedback for the results is available, the feedback may also be provided as training data. For example, if a reviewer after viewing the results indicates that the results are poor estimates, the reviewer's feedback may be provided as training data to the pose estimator.

In general, fish may be tracked over long periods of time and over short periods of time. For short-term tracking, a continuous video of the fish may be obtained by controlling a camera system so that cameras in the camera system may periodically or continuously capture images of the fish as it moves. In some cases, the camera system may be programmed to automatically track fish movement. In some cases, the camera system may be controlled manually by a user, e.g., systems administrator, to track fish movement.

For long-term tracking, periodic images of a fish may be obtained, for example, every few days, weeks, or months. Methods to identify the fish may be used to confirm the identity of a fish in an image, and update the identified fish's profile. For example, in some cases, the method to identify a fish may include extracting features from a fish image through representation learning that uses a metric loss to learn a feature extractor based on positive image samples, i.e., the same fish, and negative image samples, i.e., different fish, of the fish. In some cases, hand engineering may be used to extract features from a fish image.

The result of the feature extraction is a function mapping images of the fish to a vector in a high dimensional vector space. Each detection of a fish in an image is either a new observation, e.g., first sight, or is close to a cluster of other examples, e.g., repeat visit. Clustering algorithms, e.g. K-means or Mixture of Gaussians, may be used to compute clusters. Over time as the fish mature, the cluster may drift or expand and this evolution can be tracked.

Referring back to FIG. 7B, in some implementations, after determining the weight of an imaged fish, the system may determine if more data for the fish is requested by a user or required. If more data for the fish is requested or required, the system will repeat the operations in FIGS. 7A and 7B beginning from operation S705. If no more data for the fish is requested or required, the method for determining a fish's weight, shape, and size may be terminated.

The request for additional data for the fish may be explicit or implicit. For example, in some cases, the system may be programmed to obtain multiple sets of data to determine an average weight of a fish, and the measurements may be repeated until the requisite number of data sets has been obtained. In some cases, the system may receive a request from a user to obtain additional data for a particular fish.

Although the above-noted implementations have been described with respect to obtaining images of fish, the implementations may be implemented to obtain images of various suitable objects that live in water such as worms, parasites, and squid. It should also be appreciated that monitoring modes may be configured according to various different settings, and that a computer system may communicate with multiple cameras at the same time or at different times to execute the monitoring modes.

Embodiments and all of the functional operations and/or actions described in this specification may be implemented in digital electronic circuitry, or in computer software, firmware, or hardware, including the structures disclosed in this specification and their structural equivalents, or in combinations of one or more of them. Embodiments may be implemented as one or more computer program products, for example, one or more modules of computer program instructions encoded on a computer readable medium for execution by, or to control the operation of, data processing apparatus. The computer-readable medium may be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, for example, code that constitutes processor firmware, a protocol stack, a database management system, an operating system, or a combination of one or more of them. A propagated signal is an artificially generated signal, for example, a machine-generated electrical, optical, or electromagnetic signal that is generated to encode information for transmission to a suitable receiver apparatus.

A computer program, also known as a program, software, software application, script, or code, may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data in a single file dedicated to the program in question, or in multiple coordinated files. A computer program may be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus may also be implemented as, special purpose logic circuitry, for example, an field programmable gate array (FPGA) or an application specific integrated circuit (ASIC).

Processors suitable for the execution of a computer program include, by way of example, both general and special purpose microprocessors, and any one or more processors of any kind of digital computer. Generally, a processor will receive instructions and data from a read only memory or a random access memory or both. A processor may include any suitable combination of hardware and software.

Elements of a computer may include a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. Moreover, a computer may be embedded in another device, for example, a user device. Computer-readable media suitable for storing computer program instructions and data include all forms of non-volatile memory, media and memory devices, including by way of example, semiconductor memory devices, such as EPROM, EEPROM, and flash memory devices; magnetic disks, for example, internal hard disks or removable disks; magneto optical disks; and CD ROM and DVD-ROM disks. The processor and the memory may be supplemented by, or incorporated in, special purpose logic circuitry.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and may even be claimed as such, one or more features from a claimed combination may in some cases be excised from the combination, and the claimed combination may be directed to a sub-combination or variation of a sub-combination.

Similarly, while actions are depicted in the drawings in a particular order, this should not be understood as requiring that such actions be performed in the particular order shown or in sequential order, or that all illustrated actions be performed, to achieve desirable results. Moreover, the separation of various system components in the embodiments described above should not be understood as requiring such separation in all embodiments. The described program components and systems may generally be integrated together in a single software product or packaged into multiple software products.

The phrase one or more of and the phrase at least one of include any combination of elements. For example, the phrase one or more of A and B includes A, B, or both A and B. Similarly, the phrase at least one of A and B includes A, B, or both A and B.

Thus, particular implementations have been described. Other implementations are within the scope of the following claims. For example, the actions recited in the claims may be performed in a different order and still achieve desirable results.

What is claimed is:

1. A computer-implemented method comprising:
    determining a current time of day;
    providing, to a model that is trained to output a given set of output parameters for obtaining pictures of fish that are contained within a fish pen based in given input parameters, the input parameters including timing data that specifies the determined, current time of day;
    obtaining, from the model, a particular set of output parameters; and
    configuring one or more underwater cameras based on the particular set of output parameters.

2. The method of claim 1, wherein the input parameters include a fish type, a fish activity type, a location within the fish pen, a water current within the fish pen, or a light level within the fish pen.

3. The method of claim 1, wherein the particular set of output parameters identifies a subset of the underwater cameras that are to be used to generate the images of the fish.

4. The method of claim 1, wherein the particular set of output parameters identifies one or more camera angles associated with the underwater cameras that are to be used to generate the images of the fish.

5. The method of claim 1, comprising training the model using machine learning.

6. The method of claim 1, wherein the particular set of output of output parameters specifies a particular mode of the one or more underwater cameras, selected from among multiple modes that are pre-associated with the one or more underwater cameras.

7. The method of claim 1, wherein configuring the one or more underwater cameras comprises adjusting an orientation of one or more of the underwater cameras with respect to the fish pen.

8. A system comprising:
    one or more computing devices and one or more storage devices that store instructions which, when executed by the one or more computing devices, cause the one or more computing devices to perform operations comprising:
    determining a current time of day;
    providing, to a model that is trained to output a given set of output parameters for obtaining pictures of fish that are contained within a fish pen based in given input parameters, the input parameters including timing data that specifies the determined, current time of day;

obtaining, from the model, a particular set of output parameters; and configuring one or more underwater cameras based on the particular set of output parameters.

9. The system of claim 8, wherein the input parameters include a fish type, a fish activity type, a location within the fish pen, a water current within the fish pen, or a light level within the fish pen.

10. The system of claim 8, wherein the particular set of output parameters identifies a subset of the underwater cameras that are to be used to generate the images of the fish.

11. The system of claim 8, wherein the particular set of output parameters identifies one or more camera angles associated with the underwater cameras that are to be used to generate the images of the fish.

12. The system of claim 8, wherein the operations comprise training the model using machine learning.

13. The system of claim 8, wherein the particular set of output of output parameters specifies a particular mode of the one or more underwater cameras, selected from among multiple modes that are pre-associated with the one or more underwater cameras.

14. The system of claim 8, wherein configuring the one or more underwater cameras comprises adjusting an orientation of one or more of the underwater cameras with respect to the fish pen.

15. One or more non-transitory computer-readable storage media comprising instructions, which, when executed by one or more computing devices, cause the one or more computing devices to perform operations comprising:

determining a current time of day;

providing, to a model that is trained to output a given set of output parameters for obtaining pictures of fish that are contained within a fish pen based in given input parameters, the input parameters including timing data that specifies the determined, current time of day;

obtaining, from the model, a particular set of output parameters; and configuring one or more underwater cameras based on the particular set of output parameters.

16. The media of claim 15, wherein the input parameters include a fish type, a fish activity type, a location within the fish pen, a water current within the fish pen, or a light level within the fish pen.

17. The media of claim 15, wherein the particular set of output parameters identifies a subset of the underwater cameras that are to be used to generate the images of the fish.

18. The media of claim 15, wherein the particular set of output parameters identifies one or more camera angles associated with the underwater cameras that are to be used to generate the images of the fish.

19. The media of claim 15, wherein the operations training the model using machine learning.

20. The media of claim 15, wherein the particular set of output of output parameters specifies a particular mode of the one or more underwater cameras, selected from among multiple modes that are pre-associated with the one or more underwater cameras.

* * * * *